(12) United States Patent
Costello et al.

(10) Patent No.: US 9,078,866 B2
(45) Date of Patent: *Jul. 14, 2015

(54) METHOD FOR TREATING HYPERGLYCEMIA WITH GLP-1

(75) Inventors: Donald Costello, Bridgewater, NJ (US); Peter Richardson, Ringoes, NJ (US); Robert A. Baughman, Ridgefield, CT (US); Mark T. Marino, Long Valley, NJ (US)

(73) Assignee: MannKind Corporation, Valencia, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 13/257,284

(22) PCT Filed: Jan. 8, 2010

(86) PCT No.: PCT/US2010/020448
§ 371 (c)(1),
(2), (4) Date: Dec. 8, 2011

(87) PCT Pub. No.: WO2010/080964
PCT Pub. Date: Jul. 15, 2010

(65) Prior Publication Data
US 2012/0094905 A1    Apr. 19, 2012

Related U.S. Application Data

(63) Continuation-in-part of application No. 12/258,340, filed on Oct. 24, 2008, now Pat. No. 8,377,869.

(60) Provisional application No. 60/982,368, filed on Oct. 24, 2007, provisional application No. 60/985,620, filed on Nov. 5, 2007, provisional application No. 61/033,740, filed on Mar. 4, 2008, provisional application No. 61/052,127, filed on May 9, 2008, provisional application No. 61/143,358, filed on Jan. 8, 2009.

(51) Int. Cl.
| A61K 38/26 | (2006.01) |
|---|---|
| A61K 38/22 | (2006.01) |
| A61K 9/00 | (2006.01) |
| A61K 31/495 | (2006.01) |

(52) U.S. Cl.
CPC ........... *A61K 38/2278* (2013.01); *A61K 9/0075* (2013.01); *A61K 31/495* (2013.01); *A61K 38/26* (2013.01)

(58) Field of Classification Search
CPC ............................ A61K 38/26; A61K 31/495
USPC ........................................................ 514/7.2
See application file for complete search history.

(56) References Cited

U.S. PATENT DOCUMENTS

| 5,118,666 A | 6/1992 | Habener |
|---|---|---|
| 5,503,852 A | 4/1996 | Steiner et al. |
| 6,071,497 A | 6/2000 | Steiner et al. |
| 6,380,357 B2 | 4/2002 | Hermeling et al. |
| 6,428,771 B1 | 8/2002 | Steiner et al. |
| 6,444,226 B1 | 9/2002 | Steiner et al. |
| 7,598,222 B2 | 10/2009 | Prouty, Jr. et al. |
| 2002/0065239 A1 | 5/2002 | Caplan et al. |
| 2002/0161001 A1 | 10/2002 | Kanstrup et al. |
| 2003/0099636 A1* | 5/2003 | Epshtein et al. ........... 424/130.1 |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0121964 A1 | 6/2004 | Madar et al. |
| 2005/0043228 A1 | 2/2005 | DeFelippis et al. |
| 2005/0265927 A1 | 12/2005 | Lee |
| 2006/0040953 A1* | 2/2006 | Leone-Bay et al. ..... 514/255.02 |
| 2006/0120969 A1 | 6/2006 | Nilsson et al. |
| 2006/0239933 A1 | 10/2006 | Nilsson |
| 2008/0260838 A1* | 10/2008 | Hokenson et al. ............ 424/489 |
| 2009/0110647 A1 | 4/2009 | Richardson et al. |
| 2009/0111749 A1 | 4/2009 | Richardson et al. |

FOREIGN PATENT DOCUMENTS

| WO | 93/18754 A1 | 9/1993 |
|---|---|---|
| WO | 95/00127 A1 | 1/1995 |
| WO | 00/12116 A1 | 3/2000 |
| WO | 01/00654 A2 | 1/2001 |
| WO | 01/51071 A2 | 7/2001 |
| WO | 02/098348 A2 | 12/2002 |
| WO | WO 2004080482 A2 * | 9/2004 |
| WO | 2006/023943 A1 | 3/2006 |
| WO | 2006/059939 A1 | 6/2006 |
| WO | 2007/033316 A2 | 3/2007 |
| WO | 2007/098500 A2 | 8/2007 |

(Continued)

OTHER PUBLICATIONS

Colagiuri et al., Diabetes Care (2002) 25, 1410-1417.*
CN Office Action cited in Application No. 200880122670.3 mailed on Nov. 23, 2011.
European Search Report, Application No. 11180288.0 dated Dec. 22, 2011.
International Search Report, Application No. PCT/US2010/020448, mailed on Aug. 4, 2010.
Beers et al. "Section 2 Chapter 13—Diabetes Mellitus, The Merck Manual of Diagnosis and Therapy," Merck Research Laboratories, XP002574072, pp. 165-177, 1999.

(Continued)

*Primary Examiner* — Gyan Chandra
(74) *Attorney, Agent, or Firm* — K&L Gates LLP; Louis C. Cullman; Hal Gibson

(57) ABSTRACT

A method for treating hyperglycemia and/or diabetes in a subject is provided. In particular, the method is directed for the treatment of patients with Type 2 diabetes mellitus who have a fasting blood glucose concentration greater than about 8 mM, wherein the patient is administered a formulation comprising a GLP-1 molecule and a diketopiperazine by pulmonary inhalation with a dry powder inhalation system.

12 Claims, 20 Drawing Sheets

(56) References Cited

FOREIGN PATENT DOCUMENTS

| WO | 2007/121411 A2 | 10/2007 |
|---|---|---|
| WO | 2009/055740 A2 | 4/2009 |
| WO | 2009/055742 A2 | 4/2009 |

OTHER PUBLICATIONS

XP002574071 "Glucagon-like peptide-1 inhalation-MannKind Corporation" ADIS R&D Insight, 2009.
Russian Office Action for Application No. 201020672 issued Feb. 28, 2012.
Hui et al., "The short half-life of glucagon-like peptide-1 in plasma does not reflect its long-lasting beneficial effects", European Journal of Endocrinology (2002), 146 : 863-869.
AU Examiners Report, Application No. 2007238000, mailed Mar. 22, 2012.
Li, Jun. Chapter 15: Drug Therapy of Metabolic Diseases. Clinical Pharmacotherapy, People's Medical Publishing House, 1st. Edition, pp. 333-335 (2007).
Colagiuri et al., Are lower fasting plasma glucose levels at diagnosis of type 2 diabetes associated with improved outcomes? Diabetes Care, vol. 25, No. 8, pp. 1410-1417 (2002).
Office Action issued in connection with Russian Application No. 2010120666 mailed on Apr. 27, 2012.
Office Action issued in connection with U.S. Appl. No. 13/235,208 mailed on Jul. 18, 2013.
M. Combettes et al., Newly approved and promising antidiabetic agents. Therapie, 62(4): 293-310 (2007).
Weissberger, Mannkind: Overlooked biotech with excellent prospects (part V). http:///www.investorvillage.com/smbd.asp?=mb=2885&mn=45817&pt=msg&mid=5021385 (posted on Jun. 19, 2008, accessed on Oct. 18, 2012).
Raju et al., Naseseazines A and B: a new dimeric diketopiperazine framework from a marine-derived actinomycete, *Streptomyces* sp. Organic letters, vol. 11, No. 17, pp. 3862-3865 (2009).
Transaction History page for U.S. Appl. No. 13/235,208, filed Sep. 16, 2011.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Skyler, Pulmonary insulin: current status. Diabetes Voice, vol. 51, Issue 1, p. 23-25 (2006).
Wright et al., Inhaled Insulin: Breathing new life into diabetes therapy. Nursing, vol. 37, No. 1, p. 46-48 (2007).

\* cited by examiner

SEQUENCE LISTING

```
<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

```
<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

METHOD FOR TREATING HYPERGLYCEMIA WITH GLP-1

CROSS-REFERENCE TO RELATED APPLICATIONS

The present application is a continuation-in-part of U.S. patent application Ser. No. 11/735,957, filed Apr. 16, 2007, which claims the benefit of U.S. Provisional Application No. 60/744,882, filed Apr. 14, 2006, and is a continuation-in-part of U.S. patent application Ser. No. 10/632,878, filed Aug. 1, 2003. The entire contents of each of these applications are incorporated by reference herein.

The present application is also a continuation-in-part of U.S. patent application Ser. No. 12/258,340, filed Oct. 24, 2008, which claims the benefits of: U.S. Provisional Application No. 61/052,127, filed May 9, 2008, U.S. Provisional Application No. 61/033,740, filed Mar. 4, 2008, U.S. Provisional Application No. 60/985,620, filed Nov. 5, 2007, and U.S. Provisional Application No. 60/982,368, filed Oct. 24, 2007. The entire contents of each of these applications are incorporated by reference herein.

The present application is also a continuation-in-part of U.S. patent application Ser. No. 12/258,341, filed Oct. 24, 2008, which claims the benefit of U.S. Provisional Application No. 61/094,823, filed Sep. 5, 2008, U.S. Provisional Application No. 61/052,127, filed May 9, 2008, U.S. Provisional Application No. 61/033,740, filed Mar. 4, 2008, U.S. Provisional Application No. 61/022,274, filed Jan. 18, 2008, U.S. Provisional Application No. 60/985,620, filed Nov. 5, 2007, and U.S. Provisional Application No. 60/982,368, filed Oct. 24, 2007. The entire contents of each of these applications are incorporated by reference herein.

TECHNICAL FIELD

Disclosed herein is a method for treating hyperglycemia and/or diabetes with a glucagon-like peptide 1 (GLP-1) molecule therapy. In particular, the method comprises the administration of a GLP-1 molecule into the pulmonary circulation by oral inhalation using a dry powder drug delivery system.

BACKGROUND

Drug delivery systems for the treatment of disease which introduce active ingredients into the circulation are numerous and include oral, transdermal, subcutaneous and intravenous administration. While these systems have been used for quite a long time and can deliver sufficient medication for the treatment of many diseases, there are numerous challenges associated with these drug delivery mechanisms. In particular, the delivery of effective amounts of proteins and peptides to treat a target disease has been problematic. Many factors are involved in introducing the right amount of the active agent, for example, preparation of the proper drug delivery formulation so that the formulation contains an amount of active agent that can reach its target site(s) of action in an effective amount.

The active agent must be stable in the drug delivery formulation and the formulation should allow for absorption of the active agent into the circulation and remain active so that it can reach the site(s) of action at effective therapeutic levels. Thus, in the pharmacological arts, drug delivery systems which can deliver a stable active agent are of utmost importance.

Making drug delivery formulations therapeutically suitable for treating disease depends on the characteristics of the active ingredient or agent to be delivered to the patient. Such characteristics can include in a non-limiting manner solubility, pH, stability, toxicity, release rate, and ease of removal from the body by normal physiologic processes. For example, in oral administration, if the agent is sensitive to acid, enteric coatings have been developed using pharmaceutically acceptable materials which can prevent the active agent from being released in the low pH (acid) of the stomach. Thus, polymers that are not soluble at acidic pH are used to formulate and deliver a dose containing acid-sensitive agents to the small intestine where the pH is neutral. At neutral pH, the polymeric coating can dissolve to release the active agent which is then absorbed into the enteric systemic circulation. Orally administered active agents enter the systemic circulation and pass through the liver. In certain cases, some portion of the dose is metabolized and/or deactivated in the liver before reaching the target tissues. In some instances, the metabolites can be toxic to the patient, or can yield unwanted side effects.

Similarly, subcutaneous and intravenous administration of pharmaceutically-active agents is not devoid of degradation and inactivation. With intravenous administration of drugs, the drugs or active ingredients can also be metabolized, for example in the liver, before reaching the target tissue. With subcutaneous administration of certain active agents, including various proteins and peptides, there is additionally degradation and deactivation by peripheral and vascular tissue enzymes at the site of drug delivery and during travel through the venous blood stream. In order to deliver a dose that will yield an acceptable quantity for treating disease with subcutaneous and intravenous administration of an active agent, dosing regimes will always have to account for the inactivation of the active agent by peripheral and vascular venous tissue and ultimately the liver.

SUMMARY

Disclosed herein is a method for preventing or reducing adverse effects such as profuse sweating, nausea and vomiting, which normally are associated with the subcutaneous and intravenous administration of glucagon-like peptide 1 (GLP-1) therapy. In particular, the method comprises the administration of a GLP-1 molecule into the pulmonary circulation such as by inhalation into pulmonary alveolar capillaries using a dry powder drug delivery system.

In one embodiment, a method is provided for the treatment of hyperglycemia and/or diabetes in a patient, comprising the step of administering prandially to a patient in need of treatment an inhalable dry powder formulation, comprising a therapeutically effective amount of a GLP-1 molecule; wherein the administration does not result in at least one side effect selected from the group consisting of nausea, vomiting and profuse sweating.

In another embodiment, the patient is a mammal suffering with Type 2 diabetes mellitus. In another embodiment, the dry powder formulation comprises about 0.01 mg to about 5 mg, or 0.5 mg to about 3 mg of GLP-1 in the formulation. In some embodiments, the dry powder formulation can be administered as a single dose, or more than one dose, which can be administered in intervals depending on the patient's need. In yet another embodiment, the inhalable dry powder formulation further comprises a DPP-IV inhibitor.

In one embodiment, a method is provided for reducing glucose levels in a Type 2 diabetic patient suffering with hyperglycemia, the method comprising the step of administering to the patient in need of treatment an inhalable dry powder formulation for pulmonary administration comprising a therapeutically effective amount of GLP-1, and a diketopiperazine or pharmaceutically acceptable salt thereof.

In another embodiment, the inhalable dry powder formulation comprises a diketopiperazine. In another embodiment, the diketopiperazine is 2,5-diketo-3,6-di(4-X-aminobutyl) piperazine wherein X is selected from the group consisting of succinyl, glutaryl, maleyl, and fumaryl; or a pharmaceutically acceptable salt thereof.

In another embodiment, the GLP-1 molecule is selected from the group consisting of a native GLP-1, a GLP-1 metabolite, a GLP-1 derivative, a long acting GLP-1, a GLP-1 mimetic, an exendin, or an analog thereof, or combinations thereof and the GLP-1 molecule has at least biological activity of native GLP-1. In another embodiment, the biological activity is insulinotropic activity.

In another embodiment, the method further comprises administering to a patient a therapeutically amount of an insulin molecule. In another embodiment, the inhalable dry powder formulation comprises a GLP-1 molecule co-formulated with the insulin molecule. In yet another embodiment, the insulin molecule is administered separately as an inhalable dry powder formulation. In another embodiment the insulin is a rapid acting or a long acting insulin.

In another embodiment, the method further comprises administering a formulation comprising a long acting GLP-1 analog.

In another embodiment, the inhalable dry powder formulation lacks inhibition of gastric emptying.

In one embodiment, a kit is provided for the treatment of diabetes and/or hyperglycemia comprising: a) a medicament cartridge operably configured to fit into a dry powder inhaler and containing a dry powder formulation comprises a GLP-1 molecule, and a diketopiperazine of the formula: 2,5-diketo-3,6-di(4-X-aminobutyl)piperazine; wherein X is selected from the group consisting of succinyl, glutaryl, maleyl, and fumaryl, or salt thereof, and b) an inhalation device operably configured to receive/hold and securely engage the cartridge.

In another embodiment, a kit is provided for the treatment of hyperglycemia in a type 2 diabetic patient, which comprises a pulmonary drug delivery system, comprising: a) a medicament cartridge operably configured to fit into a dry powder inhaler and capable of containing and delivering a dry powder formulation comprising a GLP-1 molecule, and a diketopiperazine of the formula: 2,5-diketo-3,6-di(4-X-aminobutyl)piperazine; wherein X is selected from the group consisting of succinyl, glutaryl, maleyl, and fumaryl, or salt thereof, and b) an inhalation device operably configured to adapt and securely engage the cartridge and deliver the dry powder formulation to the patient in use.

In another embodiment, a method for treating hyperglycemia in a subject is provided, the method comprises administering an inhalable formulation to a subject comprising a GLP-1 molecule, wherein the subject's blood glucose levels are reduced by from about 0.1 mmol/L to about 3 mmol/L for a period of approximately four hours after administration of the inhalable formulation to the patient. In other embodiments, the inhalable formulation is administered to the Type 2 diabetic patient prandially, preprandially, post-prandially or in a fasting state. In another embodiment, the inhalable formulation comprises from about 0.01 to about 5 mg, or from about 0.02 mg to about 3 mg of GLP-1 in the formulation.

In yet another embodiment, a method of treating hyperglycemia is provided which method comprises administering to a subject having a more highly elevated fasting blood glucose concentration, for example, greater than 7 mmol/L, greater than 8 mmol/L, greater than 9 mmol/L, greater than 10 mmol/L or greater than 11 mmol/L, an inhalable dry powder formulation, comprising a therapeutically effective amount of a GLP-1 molecule and a diketopiperazine. In one embodiment, the method of treating hyperglycemia comprises administering to a subject one or more doses of an inhalable dry powder formulation comprising a GLP-1 molecule in a dry powder formulation, wherein the subject has type 2 diabetes mellitus and a blood glucose concentration greater than 7 mmol/L and the GLP-1 ranges from 0.5 mg to about 3 mg in the formulation. In one embodiment herein, the method can be applied to a subject using a formulation wherein the GLP-1 molecule to be administered is native GLP-1 or GLP-1 (7-36) amide, or a recombinant form of GLP-1, synthetic form or an analog thereof. In another embodiment, the dry powder formulation used in the method comprises a native GLP-1 or GLP-1(7-36) amide and fumaryl diketopiperazine.

In another embodiment, a method of treating hyperglycemia comprises administering to a subject having a more highly elevated, abnormal fasting blood glucose concentration, a formulation for inhalation; the formulation comprising a GLP-1 molecule and fumaryl diketopiperazine. In one embodiment, the GLP-1 molecule comprises about 10% to about 30% of the formulation and is administered by pulmonary inhalation using a dry powder inhaler. In one embodiment, an effective dosage is provided in a cartridge and can be administered in an amount ranging from about 0.01 mg to about 5 mg, or from about 0.5 mg to about 3 mg of GLP-1 in the formulation. In one embodiment, the method for treating hyperglycemia comprises administering to a subject a the dry powder formulation comprising GLP-1 and fumaryl diketopiperazine which reduces fasting blood glucose concentration by about 0.5 mmol/L to about 1.5 mmol/L in about 30 to about 45 minutes following pulmonary administration.

In one embodiment, there is provided a method for the treatment of hyperglycemia in a patient diagnosed with type 2 diabetes comprising, administering to the patient by oral inhalation an effective amount of a powder formulation comprising GLP-1 and a diketopiperazine and restoring a first-phase insulin response, or early-phase insulin secretion in the patient; wherein the patient has a blood glucose concentration greater than 7 mmol/L, greater than 9 mmol/L, greater than 10 mmol/L or greater than 11 mmol/L.

In another embodiment, a method to induce a pulsatile insulin release in a subject having type 2 diabetes is provided. The method comprises administering to a subject diagnosed with type 2 diabetes and exhibiting a blood glucose level greater than 7 mmol/L, greater than 9 mmol/L, greater than 10 mmol/L or greater than 11 mmol/L, an inhalable dry powder formulation, comprising a therapeutically effective amount of a GLP-1 molecule and a diketopiperazine; wherein the GLP-1 molecule in the dry powder formulation is administered to the patient in one or more doses, which doses are effective to induce insulin secretion from the subject's pancreatic islet B-cells upon administration of the formulation. In embodiments wherein the dry powder formulation is administered in more than one doses, the intervals between dosing depends on the patient and can range from prandially at time 0 with the first dose to about 8 hours postprandially. In one embodiment, for example, the method comprises administering to a patient a first dose of the dry powder formulation prandially and another dose of the formulation at 15, 30, 45, and/or 60 minutes postprandially. In this and other embodiments, the inhalable dry powder formulation can be provided to the patient using a dry powder inhalation system adapted with a cartridge containing the dry powder formulation.

DEFINITION OF TERMS

Figure 1:
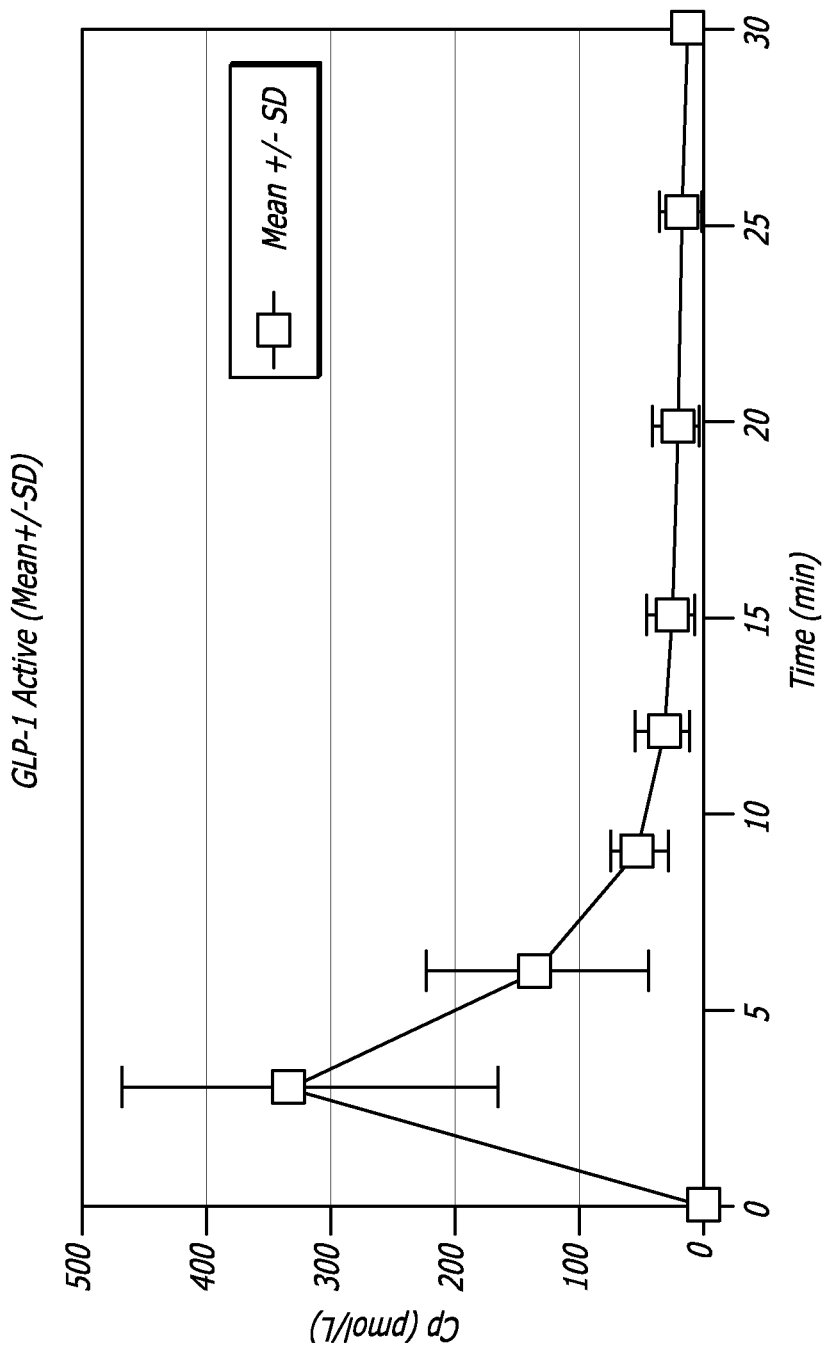
FIG. 1 depicts the mean plasma concentration of active glucagon-like peptide 1 (GLP-1) in subjects treated with an inhalable dry powder formulation containing a GLP-1 dose of 1.5 mg measured at various times after inhalation.

Prior to setting forth the invention, it may be helpful to provide an understanding of certain terms that will be used hereinafter:

Active Agents: As used herein "active agent" refers to drugs, pharmaceutical substances and bioactive agents. Active agents can be organic macromolecules including nucleic acids, synthetic organic compounds, polypeptides, peptides, proteins, polysaccharides and other sugars, fatty acids, and lipids. Peptides, proteins, and polypeptides are all chains of amino acids linked by peptide bonds. Peptides are generally considered to be less than 30 amino acid residues, but may include more. Proteins are polymers that can contain more than 30 amino acid residues. The term polypeptide as is know in the art and as used herein, can refer to a peptide, a protein, or any other chain of amino acids of any length containing multiple peptide bonds, though generally containing at least 10 amino acids. The active agents can fall under a variety of biological activity classes, such as vasoactive agents, neuroactive agents, hormones, anticoagulants, immunomodulating agents, cytotoxic agents, antibiotics, antiviral agents, antigens, and antibodies. More particularly, active agents may include, in a non-limiting manner, insulin and analogs thereof, growth hormone, parathyroid hormone (PTH), ghrelin, granulocyte macrophage colony stimulating factor (GM-CSF), glucagon-like peptide 1 (GLP-1), Texas Red, alkynes, cyclosporins, clopidogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens. In some instances, the terms "drug" and "active agent" are used interchangeably.

Analog: As used herein, an "analog" includes compounds having structural similarity to another compound. For example, the anti-viral compound acyclovir is a nucleoside analogue and is structurally similar to the nucleoside guanosine which is derived from the base guanine. Thus, acyclovir mimics guanosine (is biologically analogous with) and interferes with DNA synthesis by replacing (or competing with) guanosine residues in the viral nucleic acid and prevents translation/transcription. Thus, compounds having structural similarity to another (a parent compound) that mimic the biological or chemical activity of the parent compound are analogs. There are no minimum or maximum numbers of elemental or functional group substitutions required to qualify a compound as an analog provided the analog is capable of mimicking, in some relevant fashion, either identically, complementarily or competitively, with the biological or chemical properties of the parent compound. Analogs can be, and often are, derivatives of the parent compound (see "derivative" infra). Analogs of the compounds disclosed herein may have equal, lesser or greater activity than their parent compounds.

Derivative: As used herein, a "derivative" is a compound made from (or derived from), either naturally or synthetically, a parent compound. A derivative may be an analog (see "analog" supra) and thus may possess similar chemical or biological activity. However, unlike an analog, a derivative does not necessarily have to mimic the biological or chemical activity of the parent compound. There are no minimum or maximum numbers of elemental or functional group substitutions required to qualify a compound as a derivative. For example, while the antiviral compound ganclovir is a derivative of acyclovir, ganclovir has a different spectrum of anti-viral activity and different toxicological properties than acyclovir. Derivatives of the compounds disclosed herein may have equal, less, greater or even no similar activity when compared to their parent compounds.

Diketopiperazine: As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the sidechains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

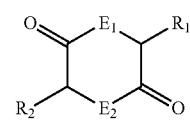

Formula 1

Diketopiperazines, in addition to making aerodynamically suitable microparticles, also facilitate the delivery of drugs by speeding absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules. Diketopiperazines may also facilitate absorption of an associated drug.

In one embodiment, the diketopiperazine is 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di (4-aminobutyl)-2,5-diketopiperazine, which can be formed by (thermal) condensation of the amino acid lysine. Exemplary derivatives include 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071, 497, and 6,331,318", each of which is incorporated herein by reference for all that it teaches regarding diketopiperazines and diketopiperazine-mediated drug delivery). The use of DKP salts is described in co-pending U.S. patent application Ser. No. 11/210,710 filed Aug. 23, 2005, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety. Further details related to adsorption of active agents onto crystalline DKP particles can be found in co-pending U.S. patent application Ser. Nos. 11/532,063 and 11/532,065 which are hereby incorporated by reference in their entirety.

Drug delivery system: As used herein, "drug delivery system" refers to a system for delivering one or more active agents.

Dry powder: As used herein, "dry powder" refers to a fine particulate composition that is not suspended or dissolved in a propellant, carrier, or other liquid. It is not meant to necessarily imply a complete absence of all water molecules.

Early phase: As used herein, "early phase" refers to the rapid rise in blood insulin concentration induced in response to a meal. This early rise in insulin in response to a meal is sometimes referred to as first-phase. In more recent sources, first-phase is sometimes used to refer to the more rapid rise in blood insulin concentration of the kinetic profile achievable with a bolus IV injection of glucose in distinction to the meal-related response.

Endocrine disease: The endocrine system is an information signal system that releases hormones from the glands to provide specific chemical messengers which regulate many and varied functions of an organism, e.g., mood, growth and development, tissue function, and metabolism, as well as sending messages and acting on them. Diseases of the endocrine system include, but are not limited to diabetes mellitus, thyroid disease, and obesity. Endocrine disease is characterized by dysregulated hormone release (a productive pituitary adenoma), inappropriate response to signalling (hypothyroidism), lack or destruction of a gland (diabetes mellitus type 1, diminished erythropoiesis in chronic renal failure), reduced responsiveness to signaling (insulin resistance of diabetes mellitus type 2) or structural enlargement in a critical site such as the neck (toxic multinodular goiter). Hypofunction of endocrine glands can occur as result of loss of reserve, hyposecretion, agenesis, atrophy, or active destruction. Hyperfunction can occur as result of hypersecretion, loss of suppression, hyperplastic, or neoplastic change, or hyperstimulation. The term endocrine disorder encompasses metabolic disorders.

Exendin: As used herein, "exendin" refers to peptides which are GLP-1 receptor agonists, including exendins 1 to 4. Carboxyl terminal fragments of exendin such as exendin[9-39], a carboxyamidated molecule, and fragments 3-39 through 9-39 are also contemplated.

Excursion: As used herein, "excursion" can refer to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating. While excursion has been described herein in terms of blood glucose, in other contexts the term may be similarly applied to other analytes.

Glucagon-like peptide-1: As used herein, the terms glucagon-like peptide-1 and GLP-1 refer to a protein or peptide having the activity of native GLP-1, a polypeptide having the amino acid sequence of SEQ ID NO.1. Also included is GLP-1(7-36)amide having the amino acid sequence of SEQ ID NO:2. GLP-1 refers to GLP-1 from any source which has the sequence of SEQ ID NO.1 including isolated, purified and/or recombinant GLP-1 produced from any source or chemically synthesizes, for example using solid phase synthesis. Also included herein are conserved amino acid substitutions of native GLP-1. For example, conservative amino acid changes may be made, which although they alter the primary sequence of the protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. In certain embodiments, the GLP-1 molecule has 80% homology to native GLP-1; 85% homology; 90% homology; 92% homology; 95% homology; 96% homology; 97% homology; 98% homology; or 99% homology to native GLP-1 while retaining at least one biological activity of native GLP-1.

GLP-1 molecules: As used herein, the term "GLP-1 molecules" refers to GLP-1 proteins, peptides, polypeptides, analogs, mimetics, derivatives, isoforms, fragments and the like which retain at least one biological activity of native GLP-1. In one embodiment, the at least one biological activity of native GLP-1 is insulinotropic activity. Such GLP-1 molecules may include naturally occurring GLP-1 polypeptides (GLP-1(7-37)OH, GLP-1(7-36)$NH_2$) and GLP-1 metabolites such as GLP-1(9-37). GLP-1 molecules also include native GLP-1, GLP-1 analogs, GLP-1 derivatives, dipeptidyl-peptidase-IV (DPP-IV)-protected GLP-1s, GLP-1 mimetics, GLP-1 peptide analogs, and biosynthetic GLP-1 analogs. Long-acting GLP-1 molecules refers to liraglutide (Novo Nordisk, Copenhagen, Denmark), exenatide (exendin-4; BYETTA®) (Amylin Inc., San Diego, Calif.), and exenatide-LAR (Eli Lilly, Indianapolis, Ind.)) that are resistant to degradation and called "incretin mimetics". Short-acting GLP-1 molecules refers to the instant compositions.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, also included are biologically active fragments of the polypeptides. The biologically active fragments are homologous to at least a portion of native GLP-1 and retain at least one biological activity of native GLP-1.

Glucose elimination rate: As used herein, "glucose elimination rate" is the rate at which glucose disappears from the blood. It is commonly determined by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL 3.5 mM), Clinically relevant hypoglycemia is defined as blood glucose concentration below 63 mg/dL or causing patient symptoms such as hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal or snack.

Metabolite: As used herein, a "metabolite" is any intermediate or product of metabolism and includes both large and small molecules. As used herein and where appropriate, the definition applies to both primary and secondary metabolites. A primary metabolite is directly involved in normal growth, development, and reproduction of living organisms. A secondary metabolite is not directly involved in those processes, but typically has important ecological function (e.g., an antibiotic).

Microparticles: As used herein, the term "microparticles" includes particles of generally 0.5 to 100 microns in diameter and particularly those less than 10 microns in diameter. Various embodiments will entail more specific size ranges. The microparticles can be assemblages of crystalline plates with irregular surfaces and internal voids as is typical of those made by pH controlled precipitation of the DKP acids. In such embodiments the active agents can be entrapped by the precipitation process or coated onto the crystalline surfaces of the microparticle. The microparticles can also be spherical shells or collapsed spherical shells comprised of DKP salts with the active agent dispersed throughout. Typically such particles can be obtained by spray drying a co-solution of the DKP and the active agent. The DKP salt in such particles can be amorphous. The forgoing descriptions should be understood as exemplary. Other forms of microparticles are contemplated and encompassed by the term.

Obesity: As used herein, "obesity" is a condition in which excess body fat has accumulated to such an extent that health may be negatively affected. Obesity is typically assessed by BMI (body mass index) with BMI of greater than 30 kg/m$^2$.

Peripheral tissue: As used herein, "peripheral tissue" refers to any connective or interstitial tissue that is associated with an organ or vessel.

Periprandial: As used herein, "periprandial" refers to a period of time starting shortly before and ending shortly after the ingestion of a meal or snack.

Postprandial: As used herein, "postprandial" refers to a period of time after ingestion of a meal or snack. As used herein, late postprandial refers to a period of time 3, 4, or more hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Preprandial: As used herein, "preprandial" refers to a period of time before ingestion of a meal or snack.

Pulmonary inhalation: As used herein, "pulmonary inhalation" is used to refer to administration of pharmaceutical preparations by inhalation so that they reach the lungs and in particular embodiments the alveolar regions of the lung. Typically inhalation is through the mouth, but in alternative embodiments in can entail inhalation through the nose.

Reduction in side effects: As used herein, the term "reduction" when used with regard to side effects, refers to a lessening of the severity of one or more side effects noticeable to the patient or a healthcare worker whose care they are under, or the amelioration of one or more side effects such that the side effects are no longer debilitating or no longer noticeable to the patient.

Side Effects: As used herein, the term "side effects" refers to unintended, and undesirable, consequences arising from active agent therapy. In a non-limiting example, common side effects of GLP-1 include, but are not limited to, nausea, vomiting and profuse sweating.

Therapeutically effective amount: As used herein, the term "therapeutically effective amount" of a composition, when administered to a human or non-human patient, to provide a therapeutic benefit such as an amelioration of symptoms, e.g., an amount effective to stimulate the secretion of endogenous insulin. In certain circumstances a patient suffering from a disorder may not present symptoms of being affected. Thus a therapeutically effective amount of a composition is also an amount sufficient to prevent the onset of symptoms of a disease.

DETAILED DESCRIPTION

Glucagon-like peptide 1 (GLP-1) has been studied as a treatment for hyperglycemia associated with Type 2 diabetes mellitus by various routes of administration. GLP-1 as disclosed in the literature is a 30 or 31 amino acid incretin hormone, released from the intestinal endocrine L-cells in response to eating fat, carbohydrates, and proteins. GLP-1 is produced as a result of proteolytic cleavage of proglucagon and the active form is identified as GLP-1(7-36) amide. Secretion of this peptide hormone is found to be impaired in individuals with type 2 diabetes mellitus making this peptide hormone a primary candidate for potential treatments of this and other related diseases.

In the non-disease state, GLP-1 is secreted from intestinal L-cells in response to orally ingested nutrients, particularly sugars. GLP-1 has effects on the gastrointestinal tract (GI) and brain including stimulating meal-induced insulin release from the pancreas. The GLP-1 effect in the pancreas is glucose dependent so the risk of GLP-1 induced hypoglycemia is minimal when the hormone is administered exogenously. GLP-1 also promotes all steps in insulin biosynthesis and directly stimulates β-cell growth, survival, and differentiation. The combination of these effects results in increased β-cell mass in pancreatic islets. Furthermore, GLP-1 receptor signaling results in a reduction of β-cell apoptosis and further contributes to increased β-cell mass.

In the gastrointestinal tract, GLP-1 as reported in the literature inhibits motility, increases the insulin secretion in response to glucose, and decreases the glucagon secretion. These effects combine to reduce postprandial glucose excursions. Experiments in rodents in which GLP-1 was given by central administration (intracerebroventricular or icy) have shown GLP-1 to inhibit food intake, suggesting that peripherally released GLP-1 can enter the systemic circulation and may have its effect on the brain. This effect may be the result of circulating GLP-1 accessing GLP-1 receptors in the brain subfornical organ and area postrema. These areas of the brain are known to be involved in the regulation of appetite and energy homeostasis. Interestingly, gastric distension activates GLP-1 containing neurons in the caudal nucleus of the solitary tract, predicting a role for centrally expressed GLP-1 as an appetite suppressant. These hypotheses are supported by studies employing the GLP-1 receptor antagonist, exendin(9-39), where opposite effects were seen. In humans, administered GLP-1 has a satiating effect, and when given by continuous subcutaneous infusion over a 6 weeks regime, patients with diabetes exhibited a reduction in appetite leading to significant reductions in body weight.

GLP-1 has also been shown to increase insulin secretion and normalize both fasting and postprandial blood glucose when given as a continuous intravenous infusion to patients with type 2 diabetes. In addition, GLP-1 infusion has been shown to lower glucose levels in patients previously treated with non-insulin oral medication and in patients requiring insulin therapy after failure on sulfonylurea therapy. However, the effects of a single subcutaneous injection of GLP-1 provided disappointing results, as is noted in the art and discussed herein below. Although high plasma levels of immunoreactive GLP-1 were achieved, insulin secretion rapidly returned to pretreatment values and blood glucose concentrations were not normalized. Repeated subcutaneous administrations were required to achieve fasting blood glucose concentrations comparable to those observed with intravenous administration. Continuous subcutaneous administration of GLP-1 for 6 weeks was shown to reduce fasting and postprandial glucose concentrations and lower HbA1c levels. The short-lived effectiveness of single subcutaneous injections of GLP-1 is related to its circulatory instability. GLP-1 is metabolized in plasma in vitro by dipeptidyl peptidase-IV (DPP-IV). GLP-1 is rapidly degraded by DPP-IV by the removal of amino acids 7 and 8 from the N-terminus. The degradation product, GLP-1(9-36) amide, is not active. DPP-4 circulates within the blood vessels and is membrane bound in the vasculature of the gastrointestinal tract and kidney and has been identified on lymphocytes in the lung.

The utility of GLP-1, and GLP-1 analogs, as a treatment for hyperglycemia associated with Type 2 diabetes mellitus has been studied for over 20 years. Clinically, GLP-1 reduces blood glucose, postprandial glucose excursions and food intake. It also increases satiety. Taken together, these actions define the unique and highly desirable profile of an anti-diabetic agent with the potential to promote weight loss. Despite these advantages, the utility of GLP-1 as a diabetes treatment is hindered because it requires administration by injection and GLP-1 has a very short circulating half-life because it is rapidly inactivated by the enzyme dipeptidyl peptidase (DPP)-IV. Thus to achieve therapeutically effective concentrations of GLP-1, higher GLP-1 doses are required. However, based on extensive literature evaluation, when active GLP-1 concentrations exceed 100 pmol/L in blood plasma, a combination of side effects/adverse effects are typically observed, including profuse sweating, nausea, and vomiting.

To address the challenge of GLP-1's limited half-life, several long-acting GLP-1 analogs have been or are currently in development. Long-acting GLP-1 analogs including liraglutide (Novo Nordisk, Copenhagen, Denmark), exenatide (exendin-4; BYETTA®) (Amylin Inc., San Diego, Calif.), and exenatide-LAR (Eli Lilly, Indianapolis, Ind.) that are resistant to degradation are called "incretin mimetics," and have been investigated in clinical trials. Exenatide is an approved therapy for type 2 diabetes. These products are formulations for subcutaneous administration, and these formulations are known to have significant limitations due to degradation in peripheral tissue, vascular tissue and/or the liver. For example, exenatide (BYETTA®), a compound with approximately 50% amino acid homology with GLP-1, has a longer circulating half-life than GLP-1. This product has been approved by the United States Food and Drug Administration (FDA) for the treatment of hyperglycemia associated with Type 2 diabetes mellitus. While the circulating half-life of exenatide is longer than that of GLP-1, it is still requires patients to inject the drug twice daily. Exenatide therapy is further complicated by a poor side effect profile including a significant incidence of nausea, pancreatitis, renal impairment. Additionally, while this long-acting therapeutic approach may provide patient convenience and facilitate compliance, the pharmacokinetic profiles for long-acting GLP-1 analogs administered by injection can be radically different from those of endogenously secreted hormones. This regimen may be effective, but does not mimic normal physiology.

While the current approaches/advances to treating diabetes and/or hyperglycemia using long-acting GLP-1 analogs administered by subcutaneous injections have been able to provide acceptable treatment for diabetes, the treatments do not mimic the body's natural physiology. For example, in healthy individuals, endogenous GLP-1 is secreted only after a meal and only in short bursts as needed. By contrast, long-acting GLP-1 analogs provide drug exposure for time periods exceeding the postprandial phase. Thus, the ideal GLP-1 therapy might be one in which the drug is administered at mealtime with exposure limited to the postprandial period. The pulmonary route of drug administration has the potential to provide such a treatment, but, to our knowledge, has not been previously explored due to the presence of DPP-IV in the lungs.

An alternative approach to prolonging the circulating half-life of GLP-1 involves the development of DPP-IV inhibitors because DPP-IV is the enzyme responsible for GLP-1 metabolism. Inhibition of DPP-IV has been shown to increase the half-life of endogenous GLP-1. Dipeptidyl peptidase IV inhibitors include vildagliptin (GALVUS®) developed by Novartis (Basel, Switzerland) and JANUVIA® (sitagliptin) developed by Merck (Whitehouse Station, N.J.).

In contrast to healthy individuals, the current methods to treat patients with hyperglycemia and type 2 diabetes use long acting GLP-1 analogs and DPP-IV inhibitors which provide drug exposure for time periods exceeding the postprandial phase. Accordingly, these current methods are not devoid of detrimental or negative side effects such as profuse sweating, nausea and vomiting, which impact on the patient's quality of life. Therefore, the inventors have identified the need to develop new methods of treatment of diseases using a drug delivery system which increases pharmacodynamic response to the drug at lower systemic exposure, while avoiding unwanted side effects. Additionally, the inventors identified the need to deliver drugs directly to the arterial circulation using a noninvasive method.

In embodiments herein, there is disclosed a method for the treatment of disease, including, endocrine disease, such as diabetes, hyperglycemia and obesity. The inventors have identified the need to deliver drugs directly to the systemic circulation, in particular, the arterial circulation in a noninvasive fashion so that the drug reaches the target organ(s) prior to returning through the venous system. This approach may paradoxically result in a higher peak target organ exposure to active agents than would result from a comparable administration via an intravenous, subcutaneous or other parenteral route. A similar advantage can be obtained versus oral administration as, even with formulations providing protection from degradation in digestive tract, upon absorption the active agent will enter the venous circulation.

In one embodiment, the drug delivery system can be used with any type of active agent that is rapidly metabolized and/or degraded by direct contact with the local degradative enzymes or other degradative mechanisms, for example oxidation, phosphorylation or any modification of the protein or peptide, in the peripheral or vascular venous tissue encountered with other routes of administration such as oral, intravenous, transdermal, and subcutaneous administration. In this embodiment, the method can comprise the step of identifying and selecting an active agent which activity is metabolized or degraded by oral, subcutaneous or intravenous administration. For example, due to lability, subcutaneous injection of GLP-1 has not led to effective levels of GLP-1 in the blood. This contrasts with peptides such as insulin which can be delivered effectively by such modes of administration.

In certain embodiments, the method of treatment of a disease or disorder comprises the step of selecting a suitable carrier for inhalation and delivering an active substance to pulmonary alveoli. In this embodiment, the carrier can be associated with one or more active agents to form a drug/carrier complex which can be administered as a composition that avoids rapid degradation of the active agent in the peripheral and vascular venous tissue of the lung. In one embodiment, the carrier is a diketopiperazine.

The method described herein can be utilized to deliver many types of active agents, including biologicals. In particular embodiments, the method utilizes a drug delivery system that effectively delivers a therapeutic amount of an active agent, including peptide hormones, rapidly into the arterial circulation. In one embodiment, the one or more active agents include, but are not limited to peptides such as glucagon-like peptide 1 (GLP-1), proteins, lipokines, small molecule pharmaceuticals, nucleic acids and the like, which is/are sensitive to degradation or deactivation; formulating the active agent into a dry powder composition comprising a diketopiperazine and delivering the active agent(s) into the systemic circulation by pulmonary inhalation using a cartridge and a dry powder inhaler. In one embodiment, the method comprises selecting a peptide that is sensitive to enzymes in the local vascular or peripheral tissue of, for example, the dermis and lungs. The present method allows the active agent to avoid or reduce contact with peripheral tissue, venous or liver metabolism/degradation. In another embodiment, for systemic delivery the active agent should not have specific receptors in the lungs.

In alternate embodiments, the drug delivery system can also be used to deliver therapeutic peptides or proteins of naturally occurring, recombinant, or synthetic origin for treating disorders or diseases, including, but not limited to adiponectin, cholecystokinin (CCK), secretin, gastrin, glucagon, motilin, somatostatin, brain natriuretic peptide (BNP), atrial natriuretic peptide (ANP), parathyroid hormone, parathyroid hormone related peptide (PTHrP), IGF-1, growth hormone releasing factor (GHRF), granulocyte-macrophage colony stimulating factor (GM-CSF), anti-IL-8 antibodies, IL-8 antagonists including ABX-IL-8; integrin beta-4 precursor (ITB4) receptor antagonist, enkephalins, nociceptin, nocistatin, orphanin FQ2, calcitonin, CGRP, angiotensin, substance P, neurokinin A, pancreatic polypeptide, neuropeptide Y, delta-sleep-inducing peptide, prostaglandings including PG-12, LTB receptor blockers including, LY29311, BIIL 284, CP105696; vasoactive intestinal peptide; triptans such as sumatriptan and lipokines such as C16:1n7 or palmitoleate. In yet another embodiment, the active agent is a small molecule drug.

In one embodiment, the method of treatment is directed to the treatment of diabetes, hyperglycemia and/or obesity using, for example, formulations comprising a GLP-1 molecule, oxyntomodulin (OXN), or peptide YY(3-36) (PYY) either alone or in combination with one another, or in combination with one or more active agents.

In an exemplary embodiment, a method for treating obesity, diabetes and/or hyperglycemia comprising administering to a patient in need of treatment a dry powder composition or formulation comprising a GLP-1 molecule, which stimulates the rapid secretion of endogenous insulin from pancreatic β-cells without causing unwanted side effects such as profuse sweating, nausea, and vomiting. In one embodiment, the method of treating disease can be applied to a patient, including a mammal, suffering with obesity, Type 2 diabetes mellitus and/or hyperglycemia at dosages ranging from about 0.02 to about 3 mg of GLP-1 in the formulation in a single dose. The method of treating hyperglycemia, diabetes, and/or obesity can be designed so that the patient can receive at least one dose of a GLP-1 formulation in proximity to a meal or snack. In this embodiment, the dose of GLP-1 can be selected depending on the patient's requirements. In one embodiment, pulmonary administration of GLP-1 can comprise a GLP-1 dose greater than 3 mg for example, in treating patients with type 2 diabetes.

In embodiments of the invention, the GLP-1 formulation is administered by inhalation such as by pulmonary administration. In this embodiment, pulmonary administration can be accomplished by providing the GLP-1 molecule in a dry powder formulation for inhalation. The dry powder formulation is a stable composition and can comprise microparticles which are suitable for inhalation and which dissolve rapidly in the lung and rapidly deliver the GLP-1 molecule to the pulmonary circulation. Suitable particle sizes for pulmonary administration can be less than 10 μm in diameter, and preferably less than 5 μm. Exemplary particle sizes that can reach the pulmonary alveoli range from about 0.5 μm to about 5.8 μm in diameter. Such sizes refer particularly to aerodynamic diameter, but often also correspond to actually physical diameter as well. Such particles can reach the pulmonary capillaries, and can avoid extensive contact with the peripheral tissue in the lung. In this embodiment, the drug can be delivered to the arterial circulation in a rapid manner and avoid degradation of the active ingredient by enzymes or other mechanisms prior to reaching its target or site of action in the body. In one embodiment, dry powder compositions for pulmonary inhalation comprising a GLP-1 molecule and FDKP can comprise microparticles wherein from about 35% to about 75% of the microparticles have an aerodynamic diameter of less than 5.8 µm.

In one embodiment, the dry powder formulation for use with the methods comprises particles comprising a GLP-1 molecule and a diketopiperazine or a pharmaceutically acceptable salt thereof. In this and other embodiments, the dry powder composition of the present invention comprises one or more GLP-1 molecules selected from the group consisting of a native GLP-1, a GLP-1 metabolite, a long acting GLP-1, a GLP-1 derivative, a GLP-1 mimetic, an exendin, or an analog thereof. GLP-1 analogs include, but are not limited to GLP-1 fusion proteins, such as albumin linked to GLP-1.

In an exemplary embodiment, the method comprises the administration of the peptide hormone GLP-1 to a patient for the treatment of hyperglycemia and/or diabetes, and obesity. The method comprises administering to a patient in need of treatment an effective amount of an inhalable composition or formulation comprising a dry powder formulation comprising a GLP-1 molecule which stimulates the rapid secretion of endogenous insulin from pancreatic β-cells without causing unwanted side effects, including, profuse sweating, nausea, and vomiting. In one embodiment, the method of treating disease can be applied to a patient, including a mammal, suffering with Type 2 diabetes mellitus and/or hyperglycemia at dosages ranging from about 0.01 mg to about 5 mg, or from about 0.5 mg to about 3 mg, or from about 0.2 mg to about 2 mg of GLP-1 in the dry powder formulation depending on the patient. In one embodiment, the patient or subject to be treated is a human. The GLP-1 molecule can be administered immediately before a meal (preprandially), at mealtime (prandially), and/or at about 15, 30, 45 and/or 60 minutes after a meal (postprandially). In one embodiment, a single dose of a GLP-1 molecule can be administered immediately before a meal and another dose can be administered after a meal. In a particular embodiment, about 0.5 mg to about 1.5 mg of GLP-1 can be administered immediately before a meal, followed by 0.5 mg to about 1.5 mg about 30 minutes after a meal. In this embodiment, the GLP-1 molecule can be formulated with inhalation particles such as a diketopiperazines with or without pharmaceutical carriers and excipients. In one embodiment, pulmonary administration of the GLP-1 formulation can provide plasma concentrations of GLP-1 greater than 100 pmol/L without inducing unwanted adverse side effects, such as profuse sweating, nausea and vomiting to the patient.

In another embodiment, a method for treating a patient including a human with type 2 diabetes and hyperglycemia is provided, the method comprises administering to the patient an inhalable GLP-1 formulation comprising a GLP-1 molecule in a concentration of from about 0.5 mg to about 3 mg in FDKP microparticles wherein the levels of glucose in the blood of the patient are reduced to fasting plasma glucose concentrations of from 85 to 70 mg/dL within about 20 min after dosing without inducing nausea or vomiting in the patient. In one embodiment, pulmonary administration of GLP-1 at concentration greater than 0.5 mg in a formulation comprising FDKP microparticles lacks inhibition of gastric emptying.

In one embodiment, the GLP-1 molecule can be administered either alone as the active ingredient in the composition, or with a dipeptidyl peptidase (DPP-IV) inhibitor such as sitagliptin or vildagliptin, or with one or more other active agents. DPP-IV is a ubiquitously expressed serine protease that exhibits postproline or alanine peptidase activity, thereby generating biologically inactive peptides via cleavage at the N-terminal region after X-proline or X-alanine, wherein X refers to any amino acid. Because both GLP-1 and GIP (glucose-dependent insulinotropic peptide) have an alanine residue at position 2, they are substrates for DPP-IV. DPP-IV inhibitors are orally administered drugs that improve glycemic control by preventing the rapid degradation of incretin hormones, thereby resulting in postprandial increases in levels of biologically active intact GLP-1 and GIP.

In this embodiment, the action of the GLP-1 molecule can be further prolonged or augmented in vivo if required, using DPP-IV inhibitors. The combination of GLP-1 and DPP-IV inhibitor therapy for the treatment of hyperglycemia and/or diabetes allows for reduction in the amount of active GLP-1 that may be needed to induce an appropriate insulin response from the β-cells in the patient. In another embodiment, the GLP-1 molecule can be combined, for example, with other molecules other than a peptide, such as, for example, metformin. In one embodiment, the DPP-IV inhibitor or other molecules, including metformin, can be administered by inhalation in a dry powder formulation together with the GLP-1 molecule in a co-formulation, or separately in its own dry powder formulation which can be administered concurrently with or prior to GLP-1 administration. In one embodiment, the DPP-IV inhibitor or other molecules, including metformin, can be administered by other routes of administration, including orally. In one embodiment, the DPP-IV inhibitor can be administered to the patient in doses ranging from about 1 mg to about 100 mg depending on the patient's need. Smaller concentration of the DPP-IV inhibitor may be used when co-administered, or co-formulated with the GLP-1 molecule. In this embodiment, the efficacy of GLP-1 therapy may be improved at reduced dosage ranges when compared to current dosage forms.

In embodiments described herein, the GLP-1 molecule can be administered at mealtime (in proximity in time to a meal or snack). In this embodiment, GLP-1 exposure can be limited to the postprandial period so it does not cause the long acting effects of current therapies. In embodiments wherein the DPP-IV inhibitor is co-administered, the DPP-IV inhibitor may be given to the patient prior to GLP-1 administration at mealtime. The amounts of DPP-IV inhibitor to be administered can range, for example, from about 0.10 mg to about 100 mg, depending on the route of administration selected. In further embodiment, one or more doses of the GLP-1 molecule can be administered after the beginning of the meal instead of, or in addition to, a dose administered in proximity to the beginning of a meal or snack. For example, one or more doses can be administered 15 to 120 minutes after the beginning of a meal, such as at 30, 45, 60, or 90 minutes.

In one embodiment, the drug delivery system can be utilized in a method for treating obesity so as to control or reduce food consumption in an animal such as a mammal. In this embodiment, patients in need of treatment or suffering with obesity are administered a therapeutically effective amount of an inhalable composition or formulation comprising a GLP-1 molecule, an exendin, oxyntomodulin, peptide YY(3-36), or combinations thereof, or analogs thereof, with or without additional appetite suppressants known in the art. In this embodiment, the method is targeted to reduce food consumption, inhibit food intake in the patient, decrease or suppress appetite, and/or control body weight.

In one embodiment, the inhalable formulation comprises a dry powder formulation comprising the above-mentioned active ingredient with a diketopiperazine, including 2,5- diketo-3,6-di(4-X-aminobutyl)piperazine; wherein X is selected from the group consisting of succinyl, glutaryl, maleyl, and fumaryl, or a salt of the diketopiperazine. In this embodiment, the inhalable formulation can comprise microparticles for inhalation comprising the active ingredient with the aerodynamic characteristics as described above. In one embodiment, the amount of active ingredient can be determined by one of ordinary skill in the art, however, the present microparticles can be loaded with various amounts of active ingredient as needed by the patient. For example, for oxyntomodulin, the microparticles can comprise from about 1% (w/w) to about 75% (w/w) of the active ingredient in the formulation. In certain embodiments, the inhalable formulations can comprise from about 10% (w/w) to about 30% (w/w) of the pharmaceutical composition and can also comprise a pharmaceutically acceptable carrier, or excipient, such as a surfactant, such as polysorbate 80. In this embodiment, oxyntomodulin can be administered to the patient from once to about four times a day or as needed by the patient with doses ranging from about 0.05 mg up to about 5 mg in the formulation. In particular embodiments, the dosage to be administered to a subject can range from about 0.1 mg to about 3.0 mg of oxyntomodulin. In one embodiment, the inhalable formulation can comprise from about 50 pmol to about 700 pmol of oxyntomodulin in the formulation.

In embodiments disclosed herein wherein PYY is used as the active ingredient, a dry powder formulation for pulmonary delivery can be made comprising from about 0.10 mg to about 3.0 mg of PYY per dose. In certain embodiments, the formulation can comprise a dry powder comprising PYY in an amount ranging from about 1% to about 75% (w/w) of the peptide in the formulation. In particular embodiments, the amount of PYY in the formulation can be 5%, 10%, 15%, or 20% (w/w) and further comprising a diketopiperazine. In one embodiment, the PYY is administered in a formulation comprising a diketopiperazine, such as FDKP or a salt thereof, including sodium salts. In certain embodiments, PYY can be administered to a subject in dosage forms so that plasma concentrations of PYY after administration are from about 4 pmol/L to about 100 pmol/L or from about 10 pmol/L to about 50 pmol/L. In another embodiment, the amount of PYY can be administered, for example, in amounts ranging from about 0.01 mg to about 30 mg, or from about 5 mg to about 25 mg in the formulation. Other amounts of PYY can be determined as described, for example, in Savage et al. Gut 1987 February; 28(2):166-70; which disclosure is incorporated by reference herein. The PYY and/or analog, or oxyntomodulin and/or analog formulation can be administered preprandially, prandially, periprandially, or postprandially to a subject, or as needed and depending on the patient physiological condition.

In one embodiment, the formulation comprising the active ingredient can be administered to the patient in a dry powder formulation by inhalation using a dry powder inhaler such as the inhaler disclosed, for example, in U.S. Pat. No. 7,305,986 and U.S. patent application Ser. No. 10/655,153 (US 2004/0182387), which disclosures are incorporated herein by reference. Repeat inhalation of dry powder formulation comprising the active ingredient can also be administered between meals and daily as needed. In some embodiments, the formulation can be administered once, twice, three or four times a day.

In still yet a further embodiment, the method of treating hyperglycemia and/or diabetes comprises the administration of an inhalable dry powder composition comprising a diketopiperazine having the formula 2,5-diketo-3,6-di(4-X-aminobutyl)piperazine, wherein X is selected from the group consisting of succinyl, glutaryl, maleyl, and fumaryl. In this embodiment, the dry powder composition can comprise a diketopiperazine salt. In still yet another embodiment of the present invention, there is provided a dry powder composition, wherein the diketopiperazine is 2,5-diketo-3,6-di-(4-fumaryl-aminobutyl)piperazine, with or without a pharmaceutically acceptable carrier, or excipient.

In certain embodiments, the method of treatment can comprise a dry powder formulation for inhalation comprising a GLP-1 molecule, wherein the GLP-1 molecule is native GLP-1, or an amidated GLP-1 molecule, wherein the amidated GLP-1 molecule is GLP-1(7-36) amide, or combinations thereof. In one embodiment, the GLP-1 can be an analog such as exenatide.

In one embodiment, a patient is administered an inhalable GLP-1 formulation in a dosing range wherein the amount of GLP-1 is from about 0.01 mg to about 5 mg, or from about 0.02 mg to about 3 mg, or from about 0.02 mg to about 2.5 mg, or from about 0.2 mg to about 2 mg of the formulation. In one embodiment, a patient with type 2 diabetes can be given a GLP-1 dose greater than 3 mg. In this embodiment, the GLP-1 can be formulated with inhalation particles such as a diketopiperazines with or without pharmaceutical carriers and excipients. In one embodiment, pulmonary administration of the GLP-1 formulation can provide plasma concentrations of GLP-1 greater than 100 pmol/L without inducing unwanted adverse side effects, such as profuse sweating, nausea and vomiting to the patient.

In another embodiment, the GLP-1 molecule can be administered with insulin as a combination therapy and given prandially for the treatment of hyperglycemia and/or diabetes, for example, Type 2 diabetes mellitus. In this embodiment, the GLP-1 molecule and insulin can be co-formulated in a dry powder formulation or administered separately to a patient in their own formulation. In one embodiment, wherein the GLP-1 molecule and insulin are co-administered, both active ingredients can be co-formulated, for example, the GLP-1 molecule and insulin can be prepared in a dry powder formulation for inhalation using a diketopiperazine particle as described above. Alternatively, the GLP-1 molecule and insulin can be formulated separately, wherein each formulation is for inhalation and comprise a diketopiperazine particle. In one embodiment the GLP-1 molecule and the insulin formulations can be admixed together in their individual powder form to the appropriate dosing prior to administration. In this embodiment, the insulin can be short-, intermediate-, or long-acting insulin and can be administered prandially.

In one embodiment for the treatment of Type 2 diabetes using co-administration of a GLP-1 molecule and insulin, an inhalable formulation of the GLP-1 molecule can be administered to a patient prandially, simultaneously, or sequentially to an inhalable formulation of insulin such as insulin/FDKP. In this embodiment, in a Type 2 diabetic, GLP-1 can stimulate insulin secretion from the patient's pancreas, which can delay disease progression by preserving β-cell function (such as by promoting β-cell growth) while prandially-administered insulin can be used as insulin replacement which mimics the body's normal response to a meal. In certain embodiments of the combination therapy, the insulin formulation can be administered by other routes of administration. In this embodiment, the combination therapy can be effective in reducing insulin requirements in a patient to maintain the euglycemic state. In one embodiment, the combination therapy can be applied to patients suffering with obesity and/or Type 2 diabetes who have had diabetes for less than 10 years and are not well controlled on diet and exercise or secretagogues. In one embodiment, the patient population for receiving GLP-1 and insulin combination therapy can be characterized by having β-cell function greater than about 25% of that of a normal healthy individual and/or, insulin resistance of less than about 8% and/or can have normal gastric emptying. In one embodiment, the inhalable GLP-1 molecule and insulin combination therapy can comprise a rapid acting insulin or a long acting insulin such as insulin glulisine (APIDRA®), insulin lispro (HUMALOG®) or insulin aspart (NOVOLOG®), or a long acting insulin such as insulin detemir (LEVEMIR®) or insulin glargine (LANTUS®), which can be administered by an inhalation powder also comprising FDKP or by other routes of administration.

In another embodiment, a combination therapy for treating type 2 diabetes can comprise administering to a patient in need of treatment an effective amount of an inhalable insulin formulation comprising an insulin and a diketopiperazine, wherein the insulin can be a native insulin peptide, a recombinant insulin peptide, and further administering to the patient a long acting insulin analog which can be provided by inhalation in a formulation comprising a diketopiperazine or by another route of administration such as by subcutaneous injection. The method can further comprise the step of administering to the patient an effective amount of a DPP IV inhibitor. In one embodiment, the method can comprise administering to a patient in need of treatment, a formulation comprising a rapid acting or long acting insulin molecule and a diketopiperazine in combination with formulation comprising a long acting GLP-1, which can be administered separately and/or sequentially. GLP-1 therapy for treating diabetes in particular, type 2 diabetes can be advantageous since administration of a GLP-1 molecule alone in a dry powder inhalable formulation or in combination with insulin or non-insulin therapies can reduce the risk of hypoglycemia.

In another embodiment, a rapid acting GLP-1 molecule and a diketopiperazine formulation can be administered in combination with a long acting GLP-1, such as exendin, for the treatment of diabetes, which can be both administered by pulmonary inhalation. In this embodiment, a diabetic patient suffering, for example, with Type 2 diabetes, can be administered prandially an effective amount of an inhalable formulation comprising a GLP-1 molecule so as to stimulate insulin secretion, while sequentially or sometime after such as from mealtime up to about 45 min, thereafter administering a dose of exendin-4. Administration of an inhalable GLP-1 molecule can prevent disease progression by preserving β-cell function while exendin-4 can be administered twice daily at approximately 10 hours apart, which can provide basal levels of GLP-1 that can mimic the normal physiology of the incretin system in a patient. Both a rapid acting GLP-1 and a long acting GLP-1 can be administered in separate, inhalable formulations. Alternatively, the long acting GLP-1 can be administered by other methods of administration including, for example, transdermally, intravenously or subcutaneously. In one embodiment, prandial administration of a short-acting and long acting GLP-1 combination may result in increased insulin secretion, greater glucagon suppression and a longer delay in gastric emptying compared to long-acting GLP-1 administered alone. The amount of long acting GLP-1 administered can vary depending on the route of administration. For example, for pulmonary delivery, the long acting GLP-1 can be administered in doses from about 0.1 mg to about 1 mg per administration, immediately before a meal or at mealtime, depending on the form of GLP-1 administered to the patient.

In one embodiment, the present method can be applied to the treatment of obesity. A therapeutically effective amount of an inhalable GLP-1 formulation can be administered to a patient in need of treatment, wherein an inhalable dry powder GLP-1 formulation comprises a GLP-1 molecule and a diketopiperazine as described above. In this embodiment, the inhalable GLP-1 formulation can be administered alone or in combination with one or more endocrine hormone and/or anti-obesity active agents for the treatment of obesity. Exemplary endocrine hormones and/or anti-obesity active agents include, but are not limited to, peptide YY, oxyntomodulin, amylin, amylin analogs such as pramlintide acetate, and the like. In one embodiment, the anti-obesity agents can be administered in a co-formulation in a dry powder inhalable composition alone or in combination with a GLP-1 molecule together or in a separate inhalable dry powder composition for inhalation. Alternatively, in the combination of a GLP-1 molecule with one or more anti-obesity agents, or agents that can cause satiety, the GLP-1 formulation can be administered in a dry powder formulation and the anti-obesity agent can be administered by alternate routes of administration. In this embodiment, a DPP-IV inhibitor can be administered to enhance or stabilize GLP-1 delivery into the pulmonary arterial circulation. In another embodiment, the DPP-IV inhibitor can be provided in combination with an insulin formulation comprising a diketopiperazine. In this embodiment, the DPP-IV inhibitor can be formulated in a diketopiperazine for inhalation or it can be administered in other formulation for other routes of administration such as by subcutaneous injection or oral administration.

In an embodiment, a kit for treating diabetes and/or hyperglycemia is provided which comprises a medicament cartridge for inhalation comprising a GLP-1 formulation and an inhalation device which is configured to adapt or securely engage the cartridge. In this embodiment, the kit can further comprise a DPP-IV inhibitor co-formulated with a GLP-1 molecule, or in a separate formulation for inhalation or oral administration as described above. In variations of this embodiment, the kit does not include the inhalation device which can be provided separately.

In one embodiment, the present combination therapy using the drug delivery system can be applied to treat metabolic disorders or syndromes. In this embodiment, the drug delivery formulation can comprise a formulation comprising a diketopiperazine and an active agent, including a GLP-1 molecule and/or a long acting GLP-1 alone or in combination with one or more active agents such as a DPP-IV inhibitor and exendin, targeted to treat the metabolic syndrome. In this embodiment, at least one of the active agents to be provided to the subject in need of treatment and who may exhibit insulin resistance can be administered by pulmonary inhalation.

In another embodiment, the pulmonary administration of an inhalable dry powder formulation comprising a GLP-1 molecule and a diketopiperazine can be used as a diagnostic tool to diagnose the level or degree of progression of type 2 diabetes in a patient afflicted with diabetes in order to identify the particular treatment regime suitable for the patient to be treated. In this embodiment, a method for diagnosing the level of diabetes progression in a patient identified as having diabetes, the method comprising administering to the patient a predetermined amount of an inhalable dry powder formulation comprising a GLP-1 molecule and a diketopiperazine and measuring the endogenous insulin production or response. The administration of the inhalable dry powder formulation comprising a GLP-1 molecule can be repeated with predetermined amounts of the GLP-1 molecule until the appropriate levels of an insulin response is obtained for that patient to determine the required treatment regime required by the patient. In this embodiment, if a patient insulin response is inadequate, the patient may require alternative therapies. Patients who are sensitive or insulin-responsive can be treated with a GLP-1 formulation comprising a diketopiperazine as a therapy. In this manner, the specific amount of GLP-1 molecule can be administered to a patient in order to achieve an appropriate insulin response to avoid hypoglycemia. In this and other embodiments, GLP-1 can induce a rapid release of endogenous insulin which mimics the normal physiology of insulin release in a patient.

In one embodiment, the present drug delivery system can be applied to treat metabolic disorders or syndromes. In this embodiment, the drug delivery formulation can comprise a formulation comprising a diketopiperazine and an active agent, including a GLP-1 molecule and/or a long acting GLP-1 alone or in combination with one or more active agents such as a DPP-IV inhibitor and exendin, targeted to treat the metabolic syndrome. In this embodiment, at least one of the active agents to be provided to the subject in need of treatment and who may exhibit insulin resistance can be administered by pulmonary inhalation.

EXAMPLES

The following examples are included to demonstrate certain embodiments of the invention. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention.

Example 1

Administration of GLP-1 in an Inhalable Dry Powder to Healthy Adult Males

GLP-1 has been shown to control elevated blood glucose in humans when given by intravenous (iv) or subcutaneous (sc) infusions or by multiple subcutaneous injections. Due to the extremely short half-life of the hormone, continuous subcutaneous infusion or multiple daily subcutaneous injections would be required to achieve clinical efficacy. Neither of these routes is practical for prolonged clinical use. Applicants have found in animal experiments that when GLP-1 was administered by inhalation, therapeutic levels could be achieved. The results of these studies can be found, for example, in U.S. patent application Ser. No. 11/735,957, the disclosure of which is incorporated by reference herein.

In healthy individuals, several of the actions of GLP-1, including reduction in gastric emptying, increased satiety, and suppression of inappropriate glucagon secretion appear to be linked to the burst of GLP-1 released as meals begin. By supplementing this early surge in GLP-1 with a formulation of GLP-1 (GLP-1(7-36)amide) and 2,5-diketo-3,6-di(4-fumaryl-aminobutyl)piperazine (FDKP) as an inhalation powder, a pharmacodynamic response, including endogenous insulin production, reduction in glucagon and glucose levels, in diabetic animals can be elicited. In addition, the late surge in native GLP-1 linked to increased insulin secretion can be mimicked by postprandial administration of GLP-1/FDKP inhalation powder.

A Phase 1a clinical trials of GLP-1/FDKP inhalation powder was designed to test the safety and tolerability of selected doses of a new inhaled glycemic control therapeutic product for the first time in human subjects. GLP-1/FDKP inhalation powder was administered using the MEDTONE® Inhaler device, previously tested. The experiments were designed to identify the safety and tolerability of various doses of GLP-1/FDKP inhalation powder by pulmonary inhalation. Doses were selected for human use based on animal safety study results from non-clinical studies in rats and primates using GLP-1/FDKP administered by inhalation as described in U.S. application Ser. No. 11/735,957, which is incorporated herein by reference.

Twenty-six subjects were enrolled into 5 cohorts to provide up to 4 evaluable subjects in each of cohorts 1 and 2 and up to 6 evaluable subjects in each of cohorts 3 to 5 who met eligibility criteria and completed the study. Each subject was dosed once with GLP-1 as GLP-1/FDKP inhalation powder at the following dose levels: cohort 1: 0.05 mg; cohort 2: 0.45 mg; cohort 3: 0.75 mg; cohort 4: 1.05 mg and cohort 5: 1.5 mg of GLP-1. Dropouts were not replaced. These dosages assumed a body mass of 70 kg. Persons of ordinary skill in the art can determine additional dosage levels based on the studies disclosed herein.

In these experiments, the safety and tolerability of ascending doses of GLP-1/FDKP inhalation powder in healthy adult male subjects were determined. The tolerability of ascending doses of GLP-1/FDKP inhalation powder were determined by monitoring pharmacological or adverse effects on variables including reported adverse events (AE), vital signs, physical examinations, clinical laboratory tests and electrocardiograms (ECG).

Additional pulmonary safety and pharmacokinetic parameters were also evaluated. Pulmonary safety as expressed by the incidence of pulmonary and other adverse events and changes in pulmonary function between Visit 1 (Screening) and Visit 3 (Follow-up) was studied. Pharmacokinetic (PK) parameters of plasma GLP-1 and serum fumaryl diketopiperazine (FDKP) following dosing with GLP-1/FDKP inhalation powder were measured as $AUC_{0-120\ min}$ plasma GLP-1 and $AUC_{0-480\ min}$ serum FDKP. Additional PK parameters of plasma GLP-1 included the time to reach maximal plasma GLP-1 concentration, $T_{max}$ plasma GLP-1; the maximal concentration of GLP-1 in plasma, $C_{max}$ plasma GLP-1, and the half of total time to reach maximal concentration of GLP-1 in plasma, $T_{1/2}$ plasma GLP-1. Additional PK parameters of serum FDKP included $T_{max}$ serum FDKP, $C_{max}$ serum FDKP, and $T_{1/2}$ serum FDKP. Clinical trial endpoints were based on a comparison of the following pharmacological and safety parameters determined in the trial subject population. Primary endpoints included the incidence and severity of reported AEs, including cough and dyspnea, nausea and/or vomiting, as well as changes from screening in vital signs, clinical laboratory tests and physical examinations. Secondary endpoints included pharmacokinetic disposition of plasma GLP-1 and serum FDKP ($AUC_{0-120\ min}$ plasma GLP-1 and $AUC_{0-480\ min}$ serum FDKP), plasma GLP-1 ($T_{max}$ plasma GLP-1, $C_{max}$ plasma GLP-1 $T_{1/2}$ plasma GLP-1); serum FDKP ($T_{max}$ serum FDKP, $C_{max}$ serum FDKP); pulmonary function tests (PFTs), and ECG.

The clinical trial consisted of 3 clinic visits: 1) One screening visit (Visit 1); 2) One treatment visit (Visit 2); and 3) One follow-up visit (Visit 3) 8-14 days after Visit 2. A single dose of GLP-1/FDKP inhalation powder was administered at Visit 2.

Five doses of GLP-1/FDKP inhalation powder (0.05, 0.45, 0.75, 1.05 and 1.5 mg of GLP-1) were assessed. To accommodate all doses, formulated GLP-1/FDKP was mixed with FDKP inhalation powder containing particles without active agent. Single-dose cartridges containing 10 mg dry powder consisting of GLP-1/FDKP inhalation powder (15% weight to weight GLP-1/FDKP) as is or mixed with the appropriate amount of FDKP inhalation powder was used to obtain the desired dose of GLP-1 (0.05 mg, 0.45 mg, 0.75 mg, 1.05 mg and 1.5 mg). The first 2 lowest dose levels were evaluated in 2 cohorts of 4 subjects each and the 3 higher dose levels were evaluated in 3 cohorts of 6 subjects each. Each subject received only 1 dose at 1 of the 5 dose levels assessed. In addition to blood drawn for GLP-1 (active and total) and FDKP measurements, samples were drawn for glucagon, glucose, insulin, and C-peptide determination. The results from these experiments are described with reference to the following figures and tables.

FIG. 1 depicts the active GLP-1 plasma concentration in cohort 5 after pulmonary administration of 1.5 mg of GLP-1 dose. The data showed that the peak GLP-1 concentration occurred prior to the first sampling point at 3 minutes, closely resembling intravenous (IV) bolus administration. GLP-1 plasma concentrations in some subjects were greater than 500 pmol/L, the assay limit. Peak active GLP-1 plasma concentrations range from about 150 pmol/L to about 500 pmol/L. Intravenous bolus administration of GLP-1 as reported in the literature (Vilsboll et al. 2000) results in ratios of total:active GLP-1 of 3.0-5.0 compared to a ratio of 1.5 in cohort 5 of this study. At comparable active concentrations the metabolite peaks were 8-9 fold greater following intravenous administration compared to pulmonary administration, suggesting that pulmonary delivery results in rapid delivery and less degradation of GLP-1.

substantially higher than physiological peak venous concentrations. However, because the half-life of GLP-1 is short (about 1-2 min), plasma concentrations of active GLP-1 fell to the physiological range by 9 min after administration. Although the peak concentrations are much higher than those seen physiologically in the venous circulation, there is evidence that local concentrations of GLP-1 may be much higher than those seen systemically.

Table 1 shows the pharmacokinetic profile of GLP-1 using a formulation comprising FDKP from this study.

FDKP pharmacokinetic parameters are also represented in Table 1 for cohorts 4 and 5. Other cohorts were not analyzed. The data also shows that mean plasma concentration of FDKP for the 1.05 mg and the 1.5 mg GLP-1 treated subjects were about 184 and 211 pmol/L, respectively. Maximal plasma FDKP concentrations were attained at about 4.5 and 6 min after administration for the respective dose with a half-life about 2 hr (127 and 123 min).

Figure 2A:
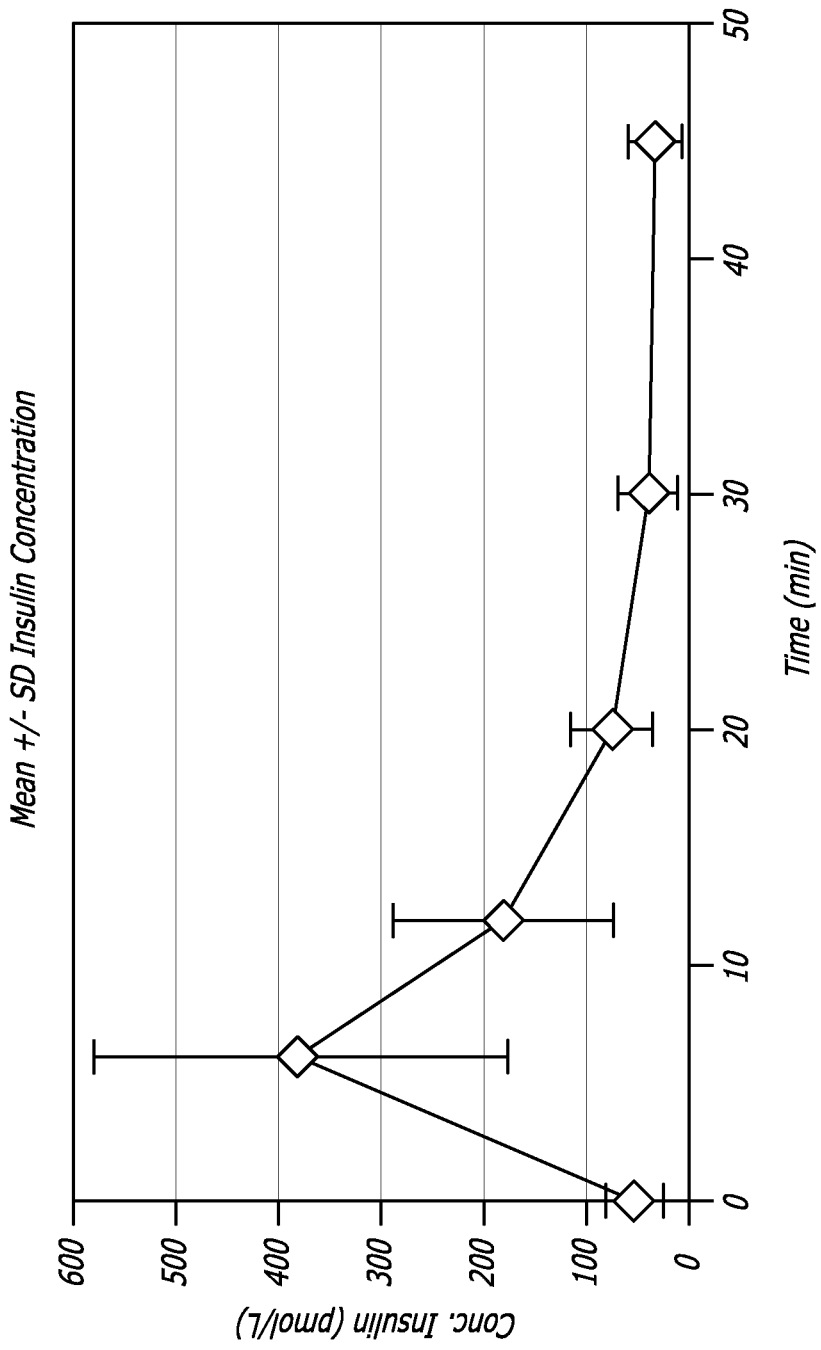
FIG. 2A depicts the mean plasma concentration of insulin in subjects treated with an inhalable dry powder formulation containing a GLP-1 dose of 1.5 mg measured at various times after inhalation.
Figure 2B:
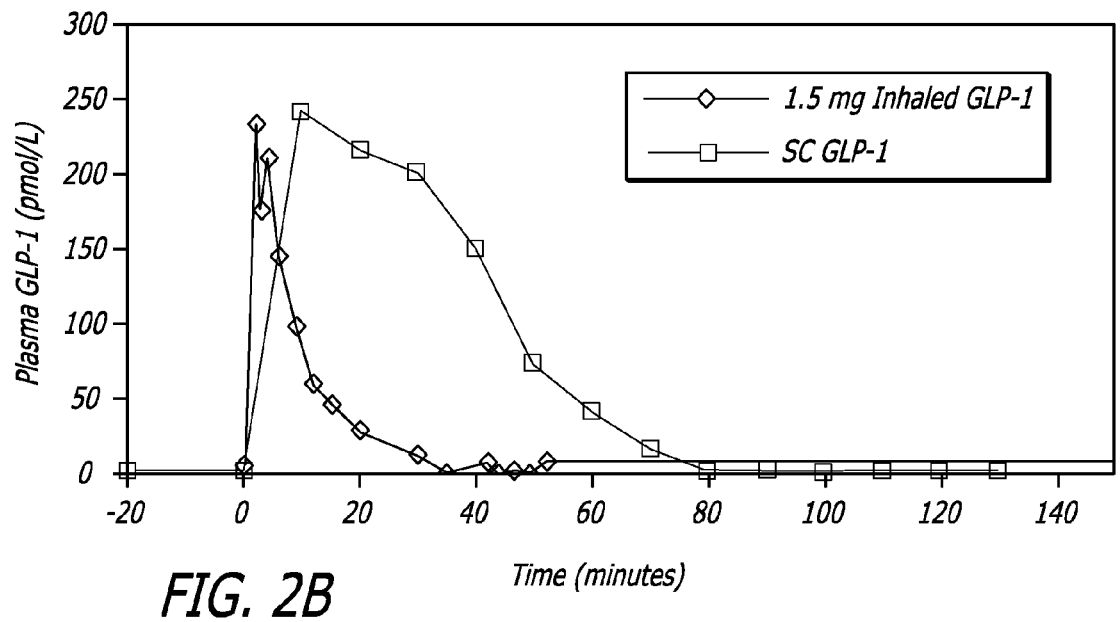
FIG. 2B depicts the plasma concentration of GLP-1 in subjects treated with an inhalable dry powder formulation containing a GLP-1 dose of 1.5 mg measured at various times after inhalation compared to subjects treated with a subcutaneous administration of GLP-1.

FIG. 2A depicts mean insulin concentrations in subjects treated with an inhalable dry powder formulation of GLP-1 at a dose of 1.5 mg. The data show the 1.5 mg GLP-1 dose induced endogenous insulin release from β-cells since insulin concentrations were detected in all subjects, and the mean peak insulin concentrations of about 380 pmol/L occurred at 6 min after dosing or earlier. The insulin release was rapid, but not sustained, since plasma insulin concentration fell rapidly after the initial response to GLP-1. FIG. 2B depicts the GLP-1

TABLE 1

| Parameter[a] | Treatment | | | | |
|---|---|---|---|---|---|
| | 0.05 mg (n = 4) | 0.45 mg (n = 4) | 0.75 mg (n = 6) | 1.05 mg (n = 6) | 1.5 mg (n = 6) |
| GLP-1[a] | | | | | |
| $AUC_{0-120}$ (min*pmol/L) | ND | n = 1 355.33 | n = 6 880.12 (195.656) | n = 4 1377.88 (634.054) | n = 4 AULQ |
| $C_{max}$ (pmol/L) | n = 4 2.828 (2.4507) | n = 4 24.630 (8.7291) | n = 6 81.172 (63.3601) | n = 6 147.613 (122.7014) | n = 6 310.700 (54.2431) |
| $t_{max}$ (min) | n = 4 3.00 (3.00, 3.00) | n = 4 3.00 (3.00, 4.02) | n = 6 3.00 (3.00, 6.00) | n = 6 3.00 (3.00, 4.98) | n = 6 3.00 (3.00, 3.00) |
| $T_{1/2}$ (min) | n = 1 6.1507 | n = 3 3.0018 (0.83511) | n = 6 5.5000 (2.96928) | n = 4 3.6489 (1.88281) | n = 6 3.9410 (1.79028) |
| FDKP | | | | | |
| $AUC_{0-120}$ (min*pmol/L) | | | | n = 6 22169.2 (4766.858) | n = 6 25594.7 (5923.689) |
| $C_{max}$ (pmol/L) | | | | n = 6 184.21 (56.893) | n = 6 210.36 (53.832) |
| $t_{max}$ (min) | | | | n = 6 4.50 (3.00, 25.02) | n = 6 6.00 (3.00, 19.98) |
| $T_{1/2}$ (min) | | | | n = 6 126.71 (11.578) | n = 6 123.82 (15.640) |

[a]All parameters are mean (SD) except tmax, which is median (range)
AULQ—Two or more subjects in the dose group had plasma concentrations of the analyte that were AULQ; NA = The pharmacokinetic profile did not meet the specifications for this profile because of the short sampling time (20 minutes); ND = Parameter could not be calculated because of insufficient data is some subjects.

Figure 2C:
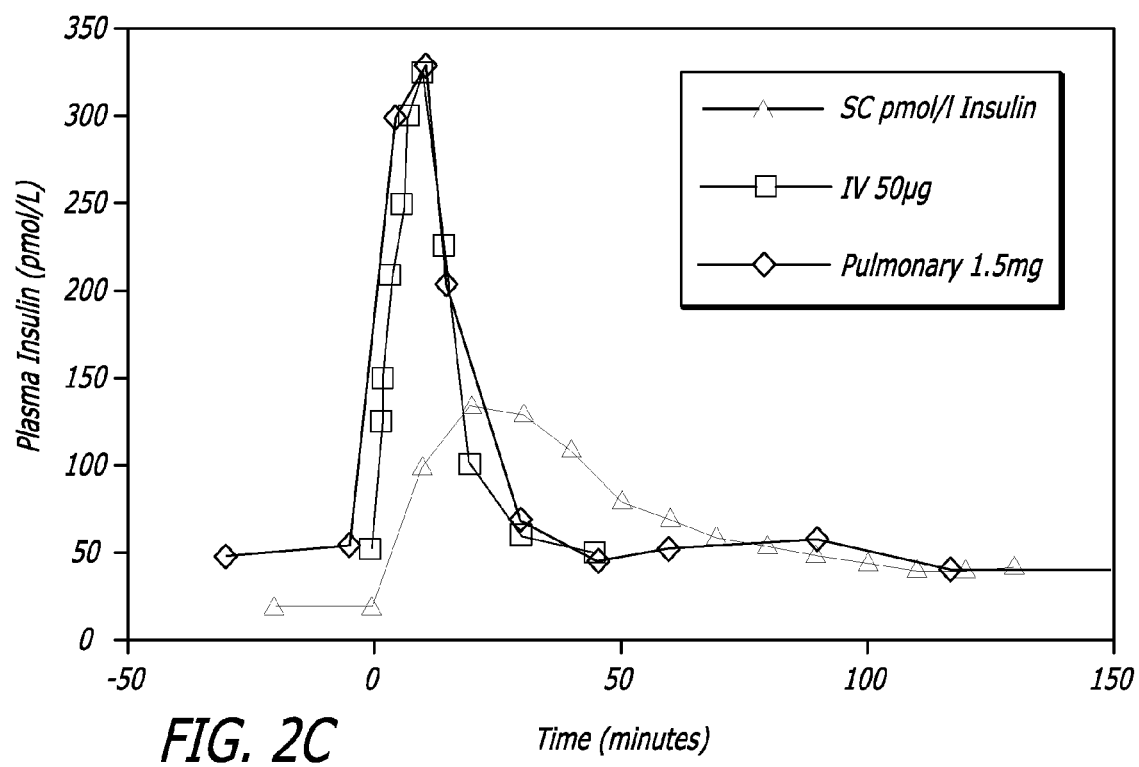
FIG. 2C depicts the plasma insulin concentration in subjects treated with an inhalable dry powder formulation containing a GLP-1 dose of 1.5 mg measured at various times after inhalation compared to subjects treated with an intravenous GLP-1 dose of 50 pg and subjects treated with a subcutaneous GLP-1 dose.

In healthy individuals, physiological post-prandial venous plasma concentrations of GLP-1 typically range from 10-20 pmol/L (Vilsboll et al. J. Clin. Endocr. & Metabolism. 88(6): 2706-13, June 2003). These levels were achieved with some subjects in cohort 2, who received 0.45 mg GLP-1. Higher doses of GLP-1 produced peak plasma GLP-1 concentrations plasma concentration of subjects treated with the 1.5 mg dose of GLP administered by pulmonary inhalation compared to subcutaneous administration of a GLP-1 dose. The data illustrates that pulmononary administration of GLP-1 occurs relatively fast and peak plasma concentration of GLP-1 occur faster than with subcutaneous administration. Additionally, pulmonary inhalation of GLP-1 leads to GLP-1 plasma concentrations returning to basal levels much faster than with subcutaneous administration. Thus the exposure of the patient to GLP-1 provided by pulmonary inhalation using the present drug delivery system is shorter in time than by subcutaneous administration and the total exposure to GLP-1 as measured by AUC is less for the inhaled insulin. FIG. 2C illustrates that pulmonary administration of a dry powder formulation of GLP-1 induces an insulin response which is similar to the response obtained after intravenous administration of GLP-1, but different in peak time and amount of endogenous insulin produced than with subcutaneous GLP-1 administration, which indicates that pulmonary administration of GLP-1 using the present formulation is more efficacious at inducing an insulin response.

Figure 3:
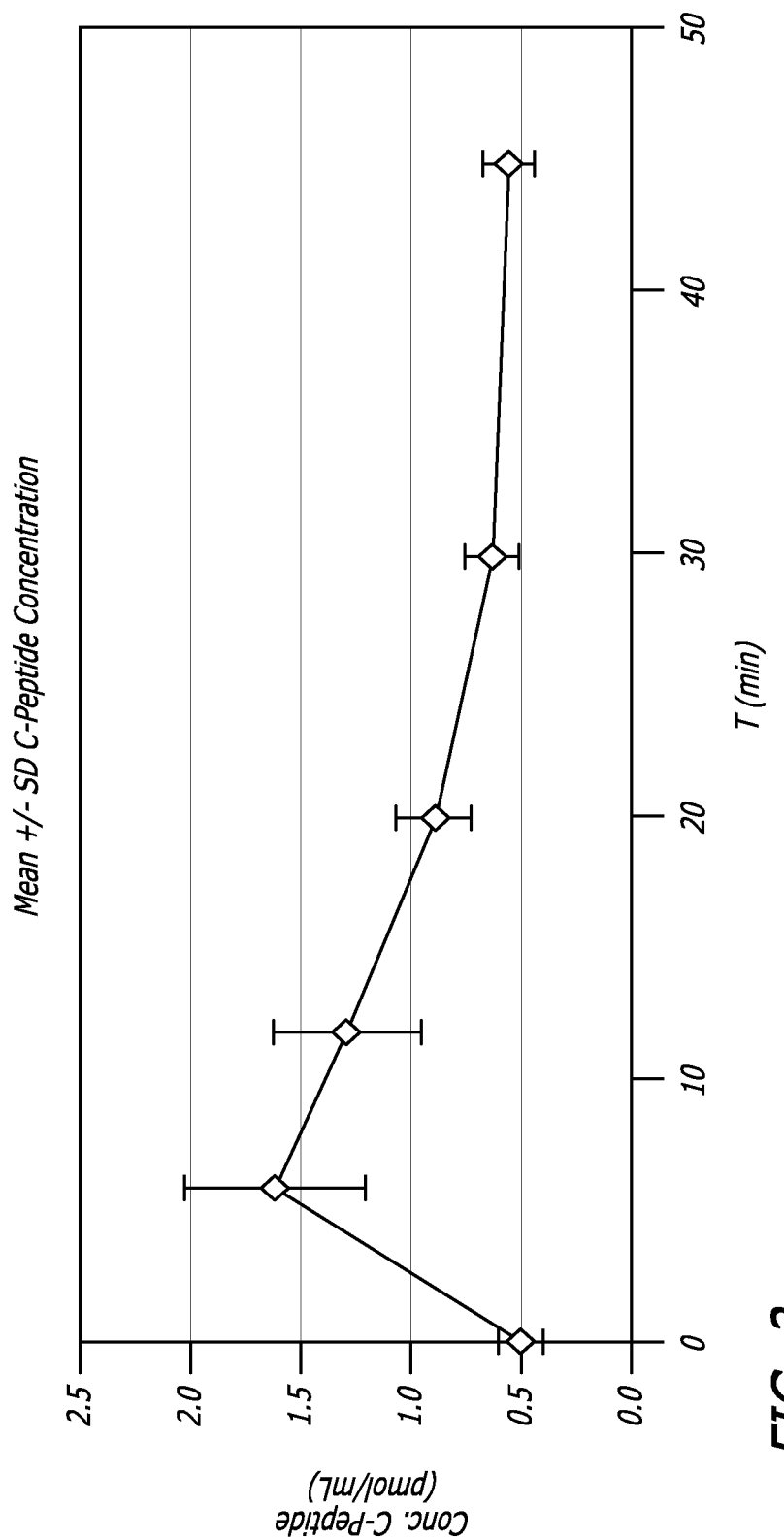
FIG. 3 depicts the mean plasma concentration of the C-peptide in subjects treated with an inhalable dry powder formulation containing a GLP-1 dose of 1.5 mg measured at various times after inhalation.

FIG. 3 depicts the plasma C-peptide concentrations in subjects treated with an inhalable dry powder formulation containing a GLP-1 dose of 1.5 mg measured at various times after inhalation. The data demonstrate that C-peptide is released following GLP-1 inhalation confirming endogenous insulin release.

Figure 4:
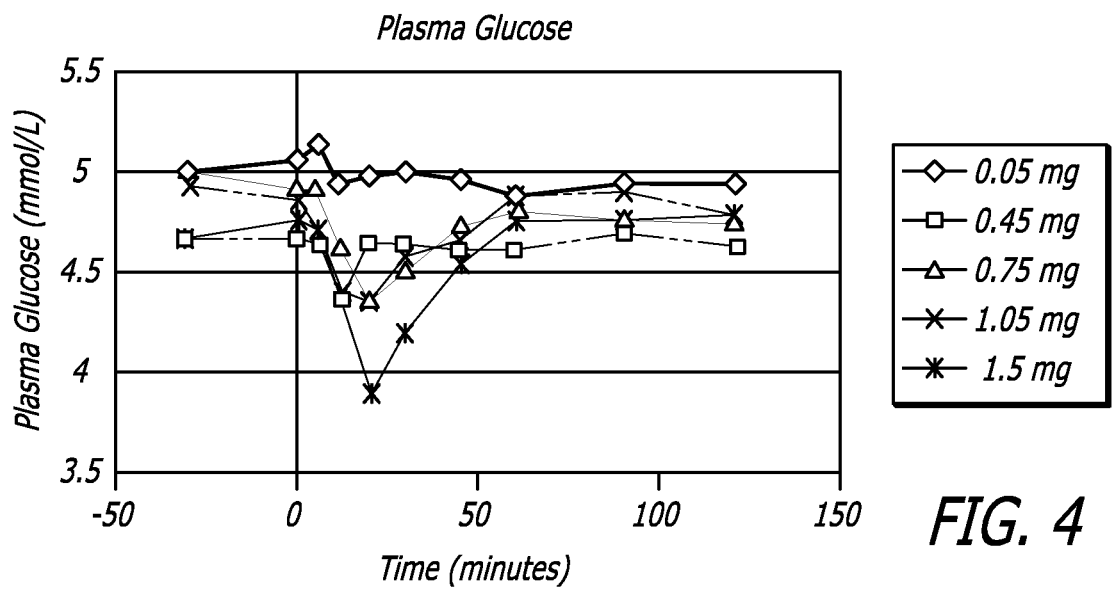
FIG. 4 depicts the mean plasma concentration of glucose in subjects treated with an inhalable dry powder formulation containing GLP-1 doses of 0.05 mg, 0.45 mg, 0.75 mg, 1.05 mg and 1.5 mg, measured at various times after inhalation.

In healthy individuals, fasting blood glucose levels range from about 3.9 mmol/L to about 5.5 mmol/L or from about 70 mg/dL to about 99 mg/dL (American Diabetes Association recommendation). FIG. 4 depicts fasting plasma glucose concentrations in subjects treated with the GLP-1 formulation containing GLP-1. Mean fasting plasma glucose (FPG) concentrations were approximately 4.7 mmol/L for the 1.5 mg GLP-1 treated subjects. GLP-1 mediated insulin release is glucose dependent. Hypoglycemia is not historically observed in euglycemic subjects. In this experiment, the data clearly show that glucose concentrations in these euglycemic healthy subjects were reduced following pulmonary administration of GLP-1. At the 1.5 mg GLP-1 dose, two of the six subjects had glucose concentrations lowered by GLP-1 to below 3.5 mmol/L, the laboratory value that defines hypoglycemia. Plasma glucose decreased more than 1.5 mol/L in two of the six subjects that received the 1.5 mg GLP-1 dose. Moreover, decreases in plasma glucose were correlated to the GLP-1 dose. The smallest decrease in glucose concentration was seen with the 0.05 mg dose, and the largest decrease was seen with the 1.5 mg dose. The three intermediate doses of GLP-1 produced roughly equal decreases in plasma glucose. The data indicate that the GLP-1 glucose-dependency was overcome based on GLP-1 concentrations above the physiologic range. Physiologic ranges for GLP-1 (7-36) amide in normal individuals has been reported to be in the range of 5-10 pmol/L during fasting, and increase rapidly after eating to 15 to 50 pmol/L (Drucker, D. and Nauck, M. The Lancet 368:1696-1705, 2006).

Figure 5:
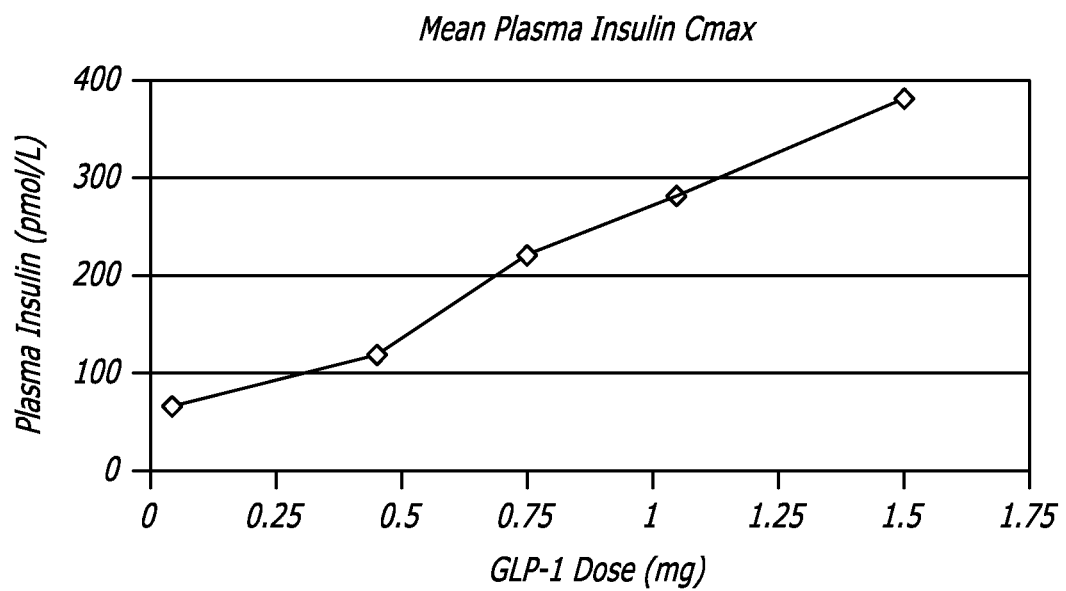
FIG. 5 depicts mean plasma insulin concentrations in patients treated with an inhalable dry powder formulation containing GLP-1 doses of 0.05 mg, 0.45 mg, 0.75 mg, 1.05 mg and 1.5 mg. The data shows that insulin secretion in response to pulmonary GLP-1 administration is dose dependent.

FIG. 5 further depicts insulin concentrations in plasma after GLP-1 pulmonary administration are dose dependent. In most subjects, the insulin release was not sustained, since plasma insulin concentration fell rapidly after the initial response to GLP-1 administration. In most subjects, the peak plasma insulin response ranged from 200-400 pmol/L with one subject exhibiting peak plasma insulin levels that exceeded 700 pmol/L. Thus, the data indicate that insulin response is GLP-1 dose dependent.

Figure 6:
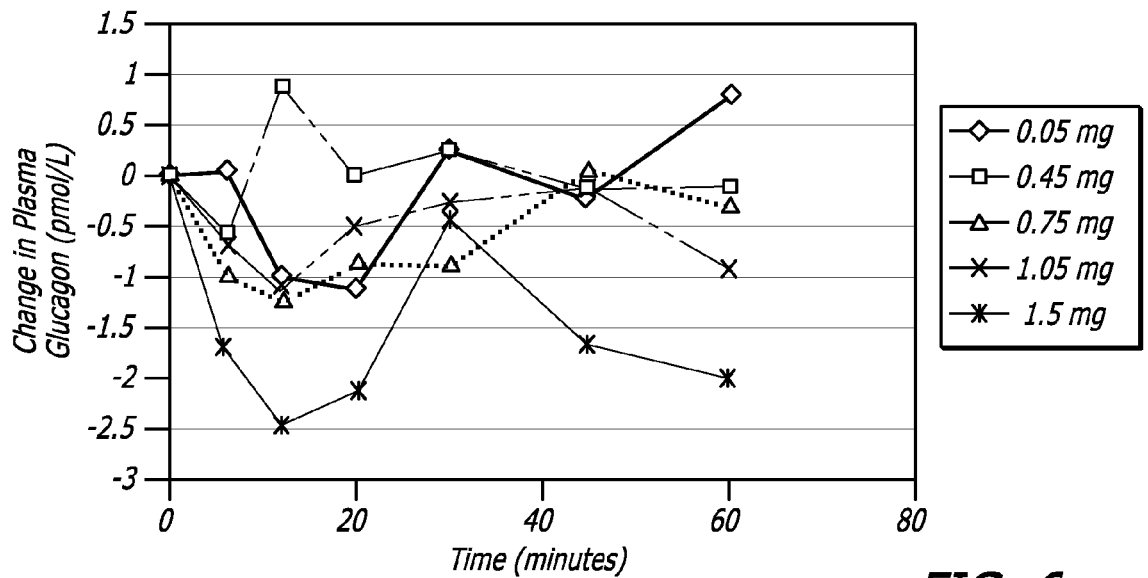
FIG. 6 depicts mean plasma glucagon concentrations in patients treated with an inhalable dry powder formulation containing GLP-1 doses of 0.05 mg, 0.45 mg, 0.75 mg, 1.05 mg and 1.5 mg.

FIG. 6 depicts glucagon concentrations in plasma after GLP-1 pulmonary administration at the various dosing groups. Baseline glucagon levels ranged from 13.2 pmol/L to 18.2 pmol/L in the various dose groups. The maximum change in plasma glucagon was seen at 12 min after dosing. The largest decrease in plasma glucagon was approximately 2.5 pmol/L and was seen in the 1.5 mg dose group. The maximum suppression of glucagon secretion was potentially underestimated because the minima did not always occur at 12 min.

Tables 2 and 3 report the adverse events or side effect symptoms recorded for the patient population in the study. The list of adverse events reported in the literature for GLP-1 administered by injection is not extensive; and those reported have been described as mild or moderate, and tolerable. The primary adverse events reported have been profuse sweating, nausea and vomiting when active GLP-1 concentrations exceed 100 pmol/L. As shown in Tables 1 and 3, and FIG. 1, pulmonary administration at doses of 1.05 mg and 1.5 mg resulted in active GLP-1 concentrations greatly exceeding 100 pmol/L without the side effects normally observed with parenteral (subcutaneous, intravenous [either bolus or infusion]) GLP-1. None of the subjects in this study reported symptoms of nausea, profuse sweating or vomiting. Subjects in Cohort 5 reached $C_{max}$ comparable to that observed with a 50 µg/kg IV bolus data (reported by Vilsboll et al. 2000), where the majority of subjects reported significant adverse events.

TABLE 2

Adverse Events

| Adverse Event | 0.05 mg (n = 4) | 0.45 mg (n = 4) | 0.75 mg (n = 6) | 1.05 mg (n = 6) | 1.5 mg (n = 6) |
|---|---|---|---|---|---|
| Cough | 3 | 1 | 3 | 5 | 5 |
| Dysphonia | 2 | — | 2 | 3 | 3 |
| Productive Cough | — | — | 1 | — | — |
| Throat Irritation | — | — | — | 1 | — |
| Headache | 1 | 1 | — | 1 | 1 |
| Dizziness | — | — | — | — | 2 |
| Dysgeusia | — | — | 1 | — | — |
| Fatigue | — | — | 1 | 1 | 1 |
| Seasonal Allergy | — | — | — | 1 | — |
| Rhinitis | — | — | — | 1 | — |
| Increased Appetite | — | — | — | — | 1 |

TABLE 3

Comparative Adverse Events of GLP-1: IV vs. Pulmonary Administration

| Adverse Events | IV[†] (16.7 µg) | IV[†*] (50 µg) | Pulmonary* (1.5 mg) |
|---|---|---|---|
| Reduced well-being | 42% | 100% | 17% |
| Nausea | 33% | 83% | 0% |
| Profuse sweating | 17% | 67% | 0% |

[†]Vilsboll et al. Diabetes Care, June 2000;
*Comparable $C_{max}$

Tables 2 and 3 show there were no serious or severe adverse events reported by any subjects in the study who received GLP-1 by pulmonary inhalation. The most commonly reported adverse events were those associated with inhalation of a dry powder, cough and throat irritation. Surprisingly, in the patients treated by pulmonary inhalation, no subject reported nausea or dysphoria, and there was no vomiting associated with any of these subjects. The inventors also found that pulmonary administration of GLP-1 in a dry powder formulation lack inhibition of gastric emptying in the above subjects (data not shown). Inhibition of gastric emptying is a commonly encountered unwanted side effect associated with injected standard formulations of GLP-1.

In summary, the clinical GLP-1/FDKP powder contained up to 15 wt % GLP-1 providing a maximum dose of 1.5 mg GLP-1 in 10 mg of powder. Andersen cascade measurements indicated that 35-70% of the particles had aerodynamic diameters <5.8 μm. A dose of 1.5 mg GLP-1 produced mean peak concentrations >300 pmol/L of active GLP-1 at the first sampling time (3 min); resulted in mean peak insulin concentrations of 375 pmol/L at the first measured time point (6 min); reduced mean fasting plasma glucose from 85 to 70 mg/dL 20 min after dosing; and was well tolerated and did not cause nausea or vomiting.

Example 2

Comparison of Pulmonary Administration of GLP-1 and Exenatide, and Subcutaneous Administration of Exenatide to Male Zucker Diabetic Fatty Rats Much effort has been expended in developing analogs of GLP-1 with longer circulating half-lives to arrive at a clinically useful treatment. As demonstrated herein pulmonary administration of GLP-1 (GLP-1(7-36)amide) also provides clinically meaningful activity. It was thus of interest to compare these two approaches.

Preparation of FDKP Particles.

Fumaryl diketopiperazine (FDKP) and polysorbate 80 were dissolved in dilute aqueous ammonia to obtain a solution containing 2.5 wt % FDKP and 0.05 wt % polysorbate 80. The FDKP solution was then mixed with an acetic acid solution containing polysorbate 80 to form particles. The particles were washed and concentrated by tangential flow filtration to achieve approximately 11% solids by weight.

Preparation of GLP-1 Stock Solution.

A 10 wt % GLP-1 stock solution was prepared in deionized water by combining 60 mg GLP-1 solids (86.6% peptide) with 451 mg deionized water. About 8 μL glacial acetic acid was added to dissolve the peptide.

Preparation of GLP-1/FDKP Particles.

A 1 g portion of the stock FDKP suspension (108 mg particles) was transferred to a 2 mL polypropylene tube. The appropriate amount of GLP-1 stock solution (Table 1) was added to the suspension and gently mixed. The pH of the suspension was adjusted from pH ~3.5 to pH ~4.5 by adding 1 μL aliquote of 50% (v/v) ammonium hydroxide. The GLP-1/FDKP particle suspension was then pelleted into liquid nitrogen and lyophilized. The dry powders were analyzed by high performance liquid chromatography (HPLC) and found comparable to theoretical values.

Preparation of Exenatide Stock Solution.

A 10 wt % exendin stock solution was prepared in 2% wt acetic acid by combining 281 mg exendin solids (88.9% peptide) with 2219 mg 2% wt acetic acid.

Preparation of Exenatide/FDKP Particles.

A 1533 mg portion of a stock FDKP particle suspension (171 mg particles) was transferred to a 4 mL glass vial. A 304 mg portion of exendin stock solution was added to the suspension and gently mixed. The pH of the suspension was adjusted from pH ~3.7 to pH ~4.5 by adding 3-5 μL aliquots of 25% (v/v) ammonium hydroxide. The exenatide/FDKP particle suspension was then pelleted into liquid nitrogen and lyophilized. The dry powders were analyzed by high performance liquid chromatography (HPLC) and found comparable to theoretical values.

Pharmacokinetic and Pharmacodynamic Assessment in Rats.

Male Zucker Diabetic Fatty (ZDF) rats (5/group) were assigned to one of four test groups. Animals were fasted overnight then administered glucose (1 g/kg) by intraperitoneal injection immediately prior to test article dosing. Animals in the control group received air by pulmonary insufflation. Animals in Group 1 received exenatide (0.3 mg) in saline (0.1 mL) by subcutaneous (SC) injections. Animals in Group 2 received 15% by weight exenatide/FDKP (2 mg) by pulmonary insufflation. Animals in Group 3 received 15% by weight GLP-1/FDKP (2 mg) by pulmonary insufflation. Blood samples were collected from the tail prior to dosing and at 15, 30, 45, 60, 90, 120, 240, and 480 min after dosing. Plasma was harvested. Blood glucose and plasma GLP-1 or plasma exenatide concentrations were determined.

Exenetide pharmacokinetics are reported in FIG. 7A. These data showed that exenatide is absorbed rapidly following insufflation of exenatide/FDKP powder. The bioavailability of the inhaled exenatide was 94% compared to subcutaneous injection. This may indicate that pulmonary administration is particularly advantageous to exenatide. The time to maximum peak circulating exenatide concentrations ($T_{max}$) was 30 min in rats receiving subcutaneous exenatide compared to <15 min in rats receiving inhaled exenatide. This $T_{max}$ was similar to that of insufflated GLP-1/FDKP (data not shown).

Figure 7:
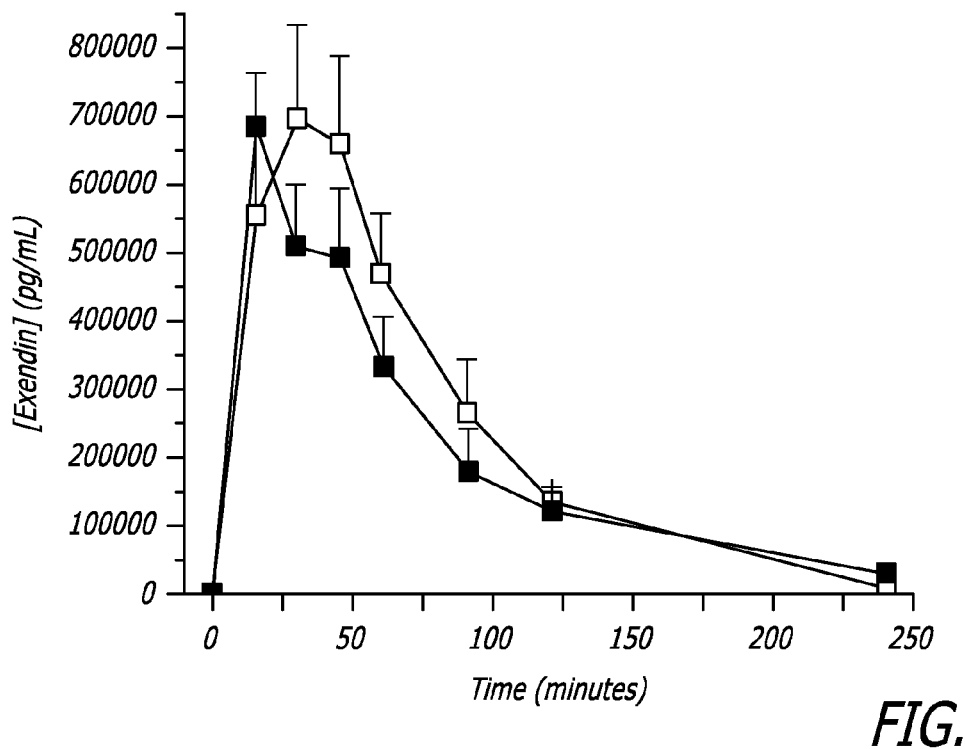
FIG. 7 depicts the mean plasma exendin concentrations in male Zucker Diabetic Fat (ZDF) rats receiving exendin-4/FDKP (fumaryl diketopiperazine) powder by pulmonary insufflation versus subcutaneous (SC) administered exendin-4. The closed squares represent the response following pulmonary insufflation of exendin-4/FDKP powder. The open squares represent the response following administration of SC exendin-4. Data are plotted as means±SD.
Figure 8:
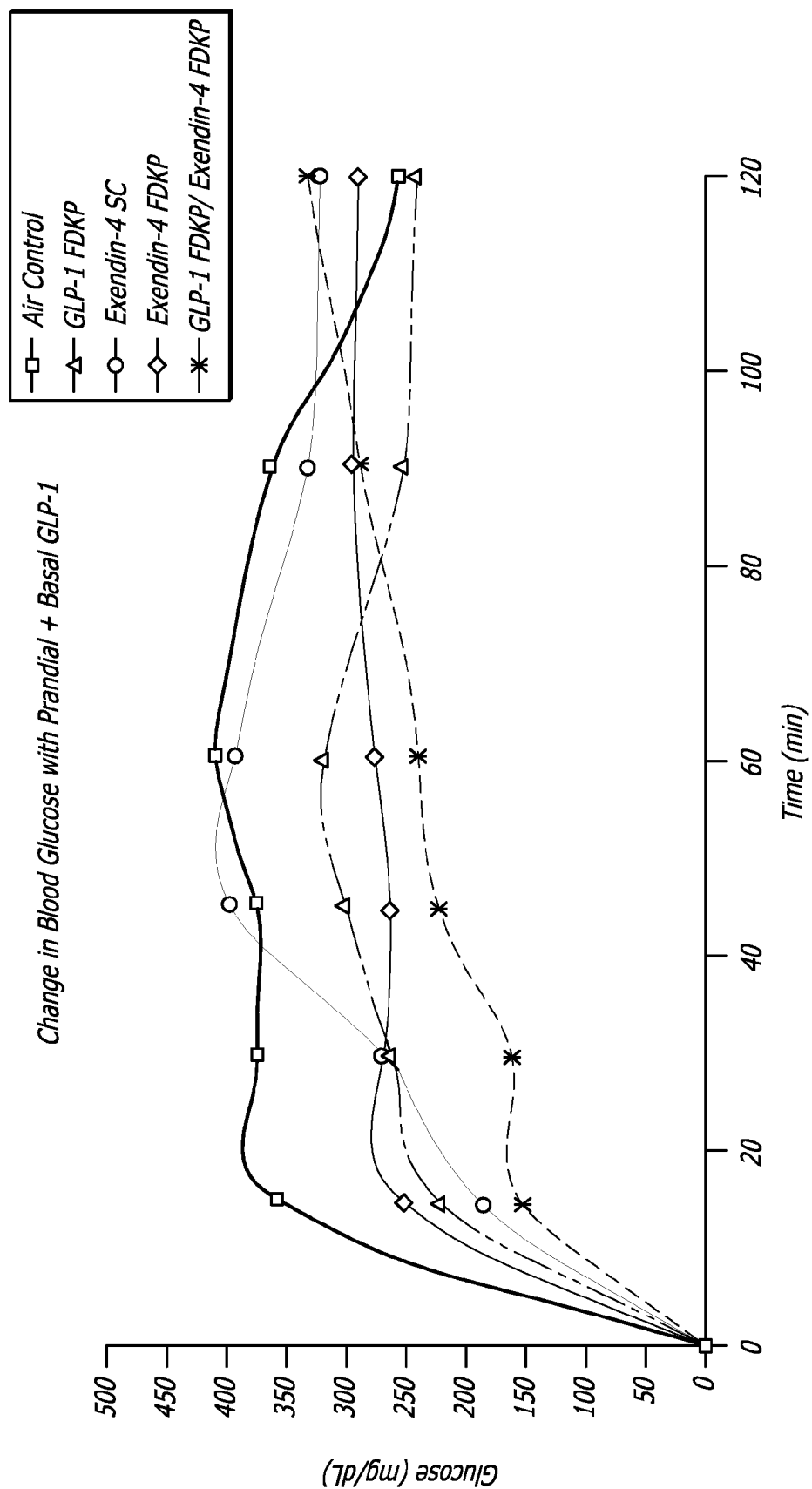
FIG. 8 depicts changes in blood glucose concentration from baseline in male ZDF rats receiving either air control, exendin-4/FDKP powder, or GLP-1/FDKP powder by pulmonary insufflation versus subcutaneously administered exendin-4. The graph also shows a combination experiment in which the rats were administered by pulmonary insufflation an inhalation powder comprising GLP-1/FDKP, followed by an inhalation powder comprising exendin-4/FDKP. In the graph, the closed diamonds represent the response following pulmonary insufflation of exendin-4/FDKP powder. The closed circles represent the response following administration of subcutaneous exendin-4. The triangles represent the response following administration of GLP-1/FDKP powder. The squares represent the response following pulmonary insufflation of air alone. The stars represent the response given by 2 mg of GLP-1/FDKP given to the rats by insufflation followed by a 2 mg exendin-4/FDKP powder administered also by insufflation.

Comparative pharmacodynamics are reported in FIG. 8. These data showed the changes in blood glucose for all four test groups. Glucose excursions following the glucose tolerance test were lower in animals receiving inhaled exenetide/FDKP as compared to animals receiving SC exenatide. Since exenatide exposure was comparable in both groups (FIG. 7), these data suggest that the shorter time to peak exenatide concentrations in the exenatide/FDKP group provided better glucose control. Additionally, glucose excursions were comparable in animals receiving either GLP-1/FDKP or exenatide/FDKP. These data are surprising because the circulating half-life of exenatide (89 min) is considerably longer than that of GLP-1 (15 min). Indeed, exenatide was developed to maximize circulating half-life for the purpose of increasing efficacy. These data suggest that the longer circulating half-life of exenatide offers no advantage in controlling hyperglycemia when using pulmonary administration. Moreover pulmonary administration of either molecule provided superior blood glucose control the SC exenatide.

FIG. 7 depicts mean plasma exendin concentrations in male ZDF rats receiving exendin-4/FDKP powder formulation administered by pulmonary insufflation versus subcutaneous exendin-4. The closed squares represent the response following pulmonary insufflation of exendin-4/FDKP powder. The open squares represent the response following administration of subcutaneously administered exendin-4. The data are plotted as±standard deviation. The data show that rats insufflated with powders providing GLP-1 doses of 0.12, 0.17, and 0.36 mg produced maximum plasma GLP-1 concentrations ($C_{max}$) of 2.3, 4.9 and 10.2 nM and exposures (AUC) of 57.1 nM·min, 92.6 nM·min, and 227.9 nM·min, respectively ($t_{max}$=10 min, $t_{1/2}$=10 min). In an intraperitoneal glucose tolerance test conducted after 4 consecutive days of dosing 0.3 mg GLP-1 per day, treated animals exhibited significantly lower glucose concentrations than the control group (p<0.05). At 30 min post-challenge, glucose increased by 47% in control animals but only 17% in treated animals.

FIG. 8 depicts the change in blood glucose from baseline in male ZDF rats receiving either air control, exendin-4/FDKP powder, or GLP-1/FDKP powder via pulmonary insufflation versus subcutaneous exendin-4 and exendin-4 administered by pulmonary insufflation. The closed diamonds represent the response following pulmonary insufflation of exendin-4/FDKP powder. The closed circles represent the response following administration of subcutaneous exendin-4. The closed triangles represent the response following administration of GLP-1/FDKP powder. The closed squares represent the response following pulmonary insufflation of air alone. The open squares represent the response given by 2 mg of GLP-1/FDKP given to the rats by insufflation followed by a 2 mg exendin-4/FDKP powder administered also by insufflation.

Example 3

Oxyntomodulin/FDKP Powder Preparation.

Oxyntomodulin, also known as glucagon-37, is a peptide consisting of 37 amino acid residues. The peptide was manufactured and acquired from American Peptide Company, Inc. of Sunnyvale, Calif. FDKP particles in suspension were mixed with an oxyntomodulin solution, then flash frozen as pellets in liquid nitrogen and lyophilized to produce sample powders.

Six powders were prepared with target peptide content between 5% and 30%. Actual peptide content determined by HPLC was between 4.4% and 28.5%. The aerodynamic properties of the 10% peptide-containing powder were analyzed using cascade impaction.

The FDKP solution was then mixed with an acetic acid solution containing polysorbate 80 to form particles. The particles were washed and concentrated by tangential flow filtration to achieve approximately 11% solids by weight.

FDKP particle suspension (1885 mg×11.14% solids=210 mg FDKP particles) was weighed into a 4 mL clear glass vial. The vial was capped and mixed using a magnetic stirrer to prevent settling. Oxyntomodulin solution (909 mg of 10% peptide in 2 wt % acetic acid) was added to the vial and allowed to mix. The final composition ratio was approximately 30:70 oxyntomodulin:FDKP particles. The oxyntomodulin/FDKP suspension had an initial pH of 4.00 which was adjusted to pH 4.48 by adding 2-10 µL increments of 1:4 (v/v) ammonium hydroxide/water. The suspension was pelleted into a small crystallization dish containing liquid nitrogen. The dish was placed in a freeze dryer and lyophilized at 200 mTorr. The shelf temperature was ramped from −45° C. to 25° C. at 0.2° C./min and then held at 25° C. for approximately 10 hours. The resultant powder was transferred to a 4 mL clear glass vial. Total yield of the powder after transfer to the vial was 309 mg (103%). Samples were tested for oxyntomodulin content by diluting the oxyntomodulin preparation in sodium bicarbonate and assaying by high pressure liquid chromatography in a Waters 2695 separations system using deionized with 0.1% trifluoroacetic acid (TFA) and acetonitrile with 0.1% TFA as mobile phases, with the wavelength detection set at 220 and 280 nm. Data was analyzed using a WATERS EMPOWER™ software program.

Pharmacokinetic and Pharmacodynamic Assessment in Rats.

Figure 9A:
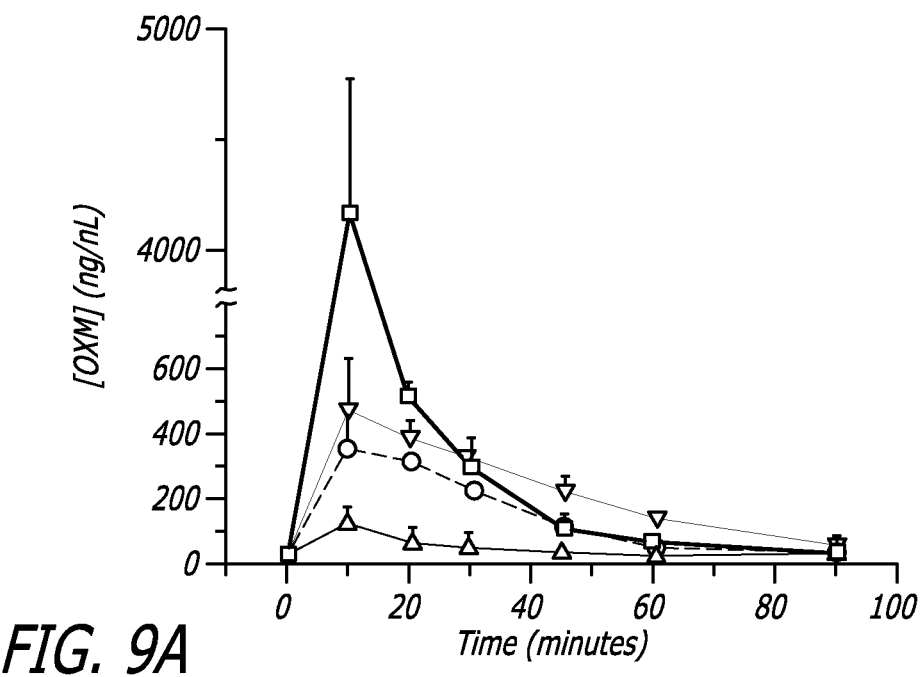
FIG. 9A depicts the mean plasma oxyntomodulin concentrations in male ZDF rats receiving oxyntomodulin/FDKP powder by pulmonary insufflation versus intravenously (IV) oxyntomodulin. The squares represent the response following IV administration of oxyntomodulin alone. The up triangles represent the response following pulmonary insufflation of 5% oxyntomodulin/FDKP powder (0.15 mg oxyntomodulin). The circles represent the response following pulmonary insufflation of 15% oxyntomodulin/FDKP powder (0.45 mg oxyntomodulin). The down triangles represent the response following pulmonary insufflation of 30% oxyntomodulin/FDKP powder (0.9 mg oxyntomodulin). Data are plotted as means±SD.

Male ZDF rats (10/group) were assigned to one of four groups. Animals in the one group received oxyntomodulin by intravenous injection. Animals in the other three groups received 5% oxyntomodulin/FDKP powder (containing 0.15 mg oxyntomodulin), 15% oxyntomodulin/FDKP powder (containing 0.45 mg oxyntomodulin), or 30% oxyntomodulin/FDKP powder (containing 0.9 mg oxyntomodulin) by pulmonary insufflation. Blood samples were collected from the tail prior to dosing and at various times after dosing for measurement of plasma oxyntomodulin concentrations (FIG. 9A). Food consumption was also monitored at various times after dosing with oxyntomodulin (FIG. 9B).

FIG. 9A is a graph comparing the plasma concentrations of oxyntomodulin following administration of an inhalable dry powder formulation at various amounts in male ZDF rats and control rats receiving oxyntomodulin by intravenous injection. These data show that oxyntomodulin is absorbed rapidly following insufflation of oxyntomodulin/FDKP powder. The time to maximum peak circulating oxyntomodulin concentrations ($T_{max}$) was less than 15 min in rats receiving inhaled oxyntomodulin. This study shows that the half life of oxyntomodulin is from about 22 to about 25 min after pulmonary administration.

Figure 9B:
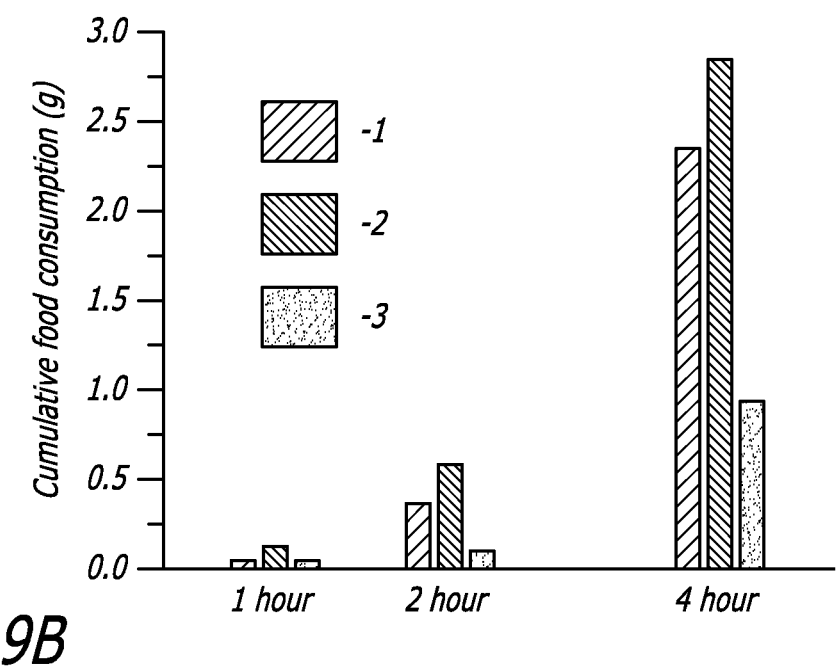
FIG. 9B depicts the cumulative food consumption in male ZDF rats receiving 30% oxyntomodulin/FDKP powder (0.9 mg oxyntomodulin) by pulmonary insufflation (1); oxyntomodulin alone (1 mg oxyntomodulin) by IV injection (2); or air control (3).

FIG. 9B is a bar graph showing cumulative food consumption in male ZDF rats treated with intravenous oxyntomodulin or oxyntomodulin/FDKP powder administered by pulomonary insufflation compared to control animals receiving an air stream. The data show that pulmonary administration of oxyntomodulin/FDKP reduced food consumption to a greater extent than either intravenous oxyntomodulin or air control with a single dose.

In a similar set of experiments, rats received an air stream as control (Group 1) or 30% oxyntomodulin/FDKP powder by pulmonary insufflation. Rats administered oxyntomodulin/FDKP inhalation powder received doses of either 0.15 mg oxyntomodulin (as 0.5 mg of oxyntomodulin/FDKP powder; Group 2), 0.45 mg oxyntomodulin (as 1.5 mg of oxyntomodulin/FDKP powder, Group 3) or 0.9 mg oxyntomodulin (as 3 mg of oxyntomodulin/FDKP powder, Group 4) prepared as described above. The studies were conducted in ZDF rats fasted for 24 hr prior to the start of the experiment. Rats were allowed to eat after receiving the experimental dose. A predetermined amount of food was given to the rats and the amount of food the rats consumed was measured at various times after the start of the experiment. The oxyntomodulin/FDKP dry powder formulation was administered to the rats by pulmonary insufflation and food measurements and blood samples were taken at various points after dosing.

Figure 10A:
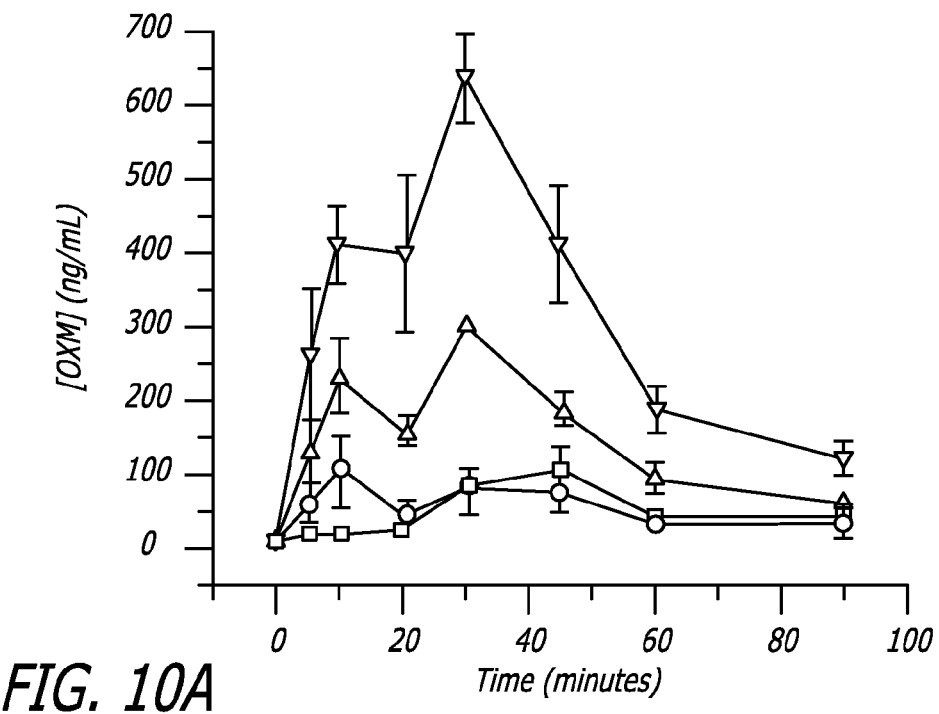
FIG. 10A depicts the mean plasma oxyntomodulin concentrations in male ZDF rats receiving oxyntomodulin/FDKP powder by pulmonary insufflation versus air control. The squares represent the response following administration of air control. The circles represent the response following pulmonary insufflation of oxyntomodulin/FDKP powder (0.15 mg oxyntomodulin). The up triangles represent the response following pulmonary insufflation of oxyntomodulin/FDKP powder (0.45 mg oxyntomodulin). The down triangles represent the response following pulmonary insufflation of oxyntomodulin/FDKP powder (0.9 mg oxyntomodulin). Data are plotted as means±SD.
Figure 10B:
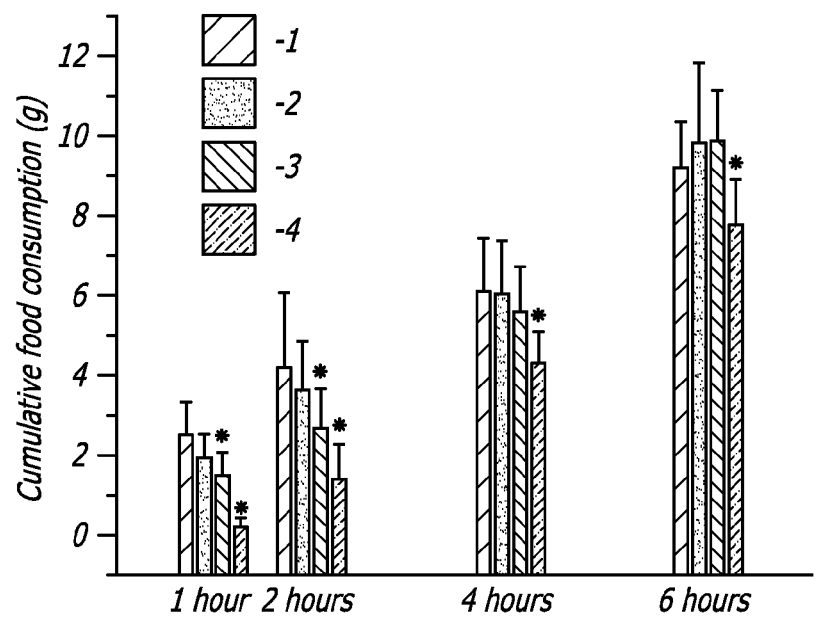
FIG. 10B depicts data from experiments showing cumulative food consumption in male ZDF rats receiving 30% oxyntomodulin/FDKP powder at varying doses including 0.15 mg oxyntomodulin (1); 0.45 mg oxyntomodulin (2); or 0.9 mg oxyntomodulin (3) by pulmonary insufflation compared to air control (4). Data are plotted as means±SD. An asterisk (*) denotes statistical significance.

FIGS. 10A and 10B show circulating oxyntomodulin concentrations for all test animals and the change in food consumption from control, respectively. Rats given oxyntomodulin consumed significantly less food than the control rats for up to 6 hr after dosing. Higher doses of oxyntomodulin appeared to suppress appetite more significantly that the lower doses indicating that appetite suppression is dose dependent, as the rats given the higher dose consumed the least amount of food at all time points measured after dosing.

Maximal concentrations of oxyntomodulin in blood were detected at 10 to 30 min and that maximal concentration of oxyntomodulin was dose dependent as the rats receiving 1.5 mg of oxyntomodulin had a maximal plasma concentration of 311 µg/mL and rats receiving 3 mg of oxyntomodulin had a maximal plasma concentration of 660 µg/mL. The half-life ($t_{1/2}$) of oxyntomodulin in the Sprague Dawley rats after administration by pulmonary insufflation ranged from about 25 to 51 min.

Example 4

Administration of GLP-1 in an Inhalable Dry Powder to Type 2 Diabetic Patients

A Phase 1 clinical trial of GLP-1/FDKP inhalation powder was conducted in patients suffering with Type 2 diabetes mellitus to assess the glucose levels of the patients before and after treatment with GLP-1 dry powder formulation by pulmonary inhalation. These studies were conducted according to Example 1 and as described herein. GLP-1 inhalation powder was prepared as described in U.S. patent application Ser. No. 11/735,957, which disclosure is incorporated herein by reference. The dry inhalation powder contained 1.5 mg of human GLP-1(7-36) amide in a total of 10 mg dry powder formulation containing FDKP in single dose cartridge. For this study, 20 patients with Type 2 diabetes, including adult males and postmenopausal females, were fasted overnight and remained fasted for a period of 4 hr after GLP-1 inhalation powder administration. The dry powder formulation was administered using the MEDTONE® dry powder inhaler (MannKind Corporation), and described in U.S. patent application Ser. No. 10/655,153, which disclosure is incorporated herein by reference in its entirety.

Blood samples for assessing serum glucose levels from the treated patients were obtained at 30 min prior to dosing, at dosing (time 0), and at approximately 2, 4, 9, 15, 30, 45, 60, 90, 120 and 240 min following GLP-1 administration. The serum glucose levels were analyzed for each sample.

Figure 11:
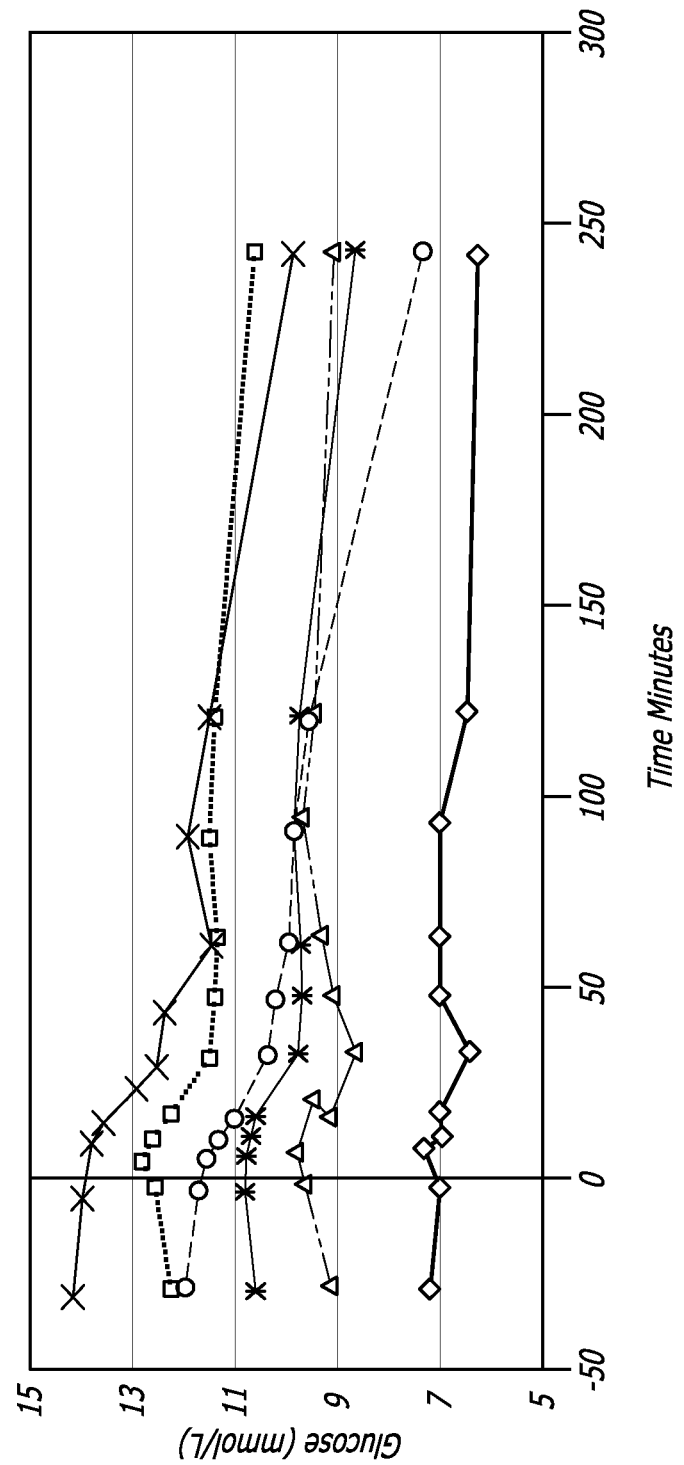
FIG. 11 depicts the glucose values obtained from six fasted Type 2 diabetic patients following administration of a single dose of an inhalable dry powder formulation containing GLP-1 at various time points.

FIG. 11 is a graph showing the results of these studies and depicts the glucose values obtained from six fasted patients with Type 2 diabetes following administration of a single dose of an inhalable dry powder formulation containing GLP-1 at various time points. The glucose values for all six patients decreased following administration of GLP-1 and remained depressed for at least 4 hrs after administration at the termination of the study.

Figure 12:
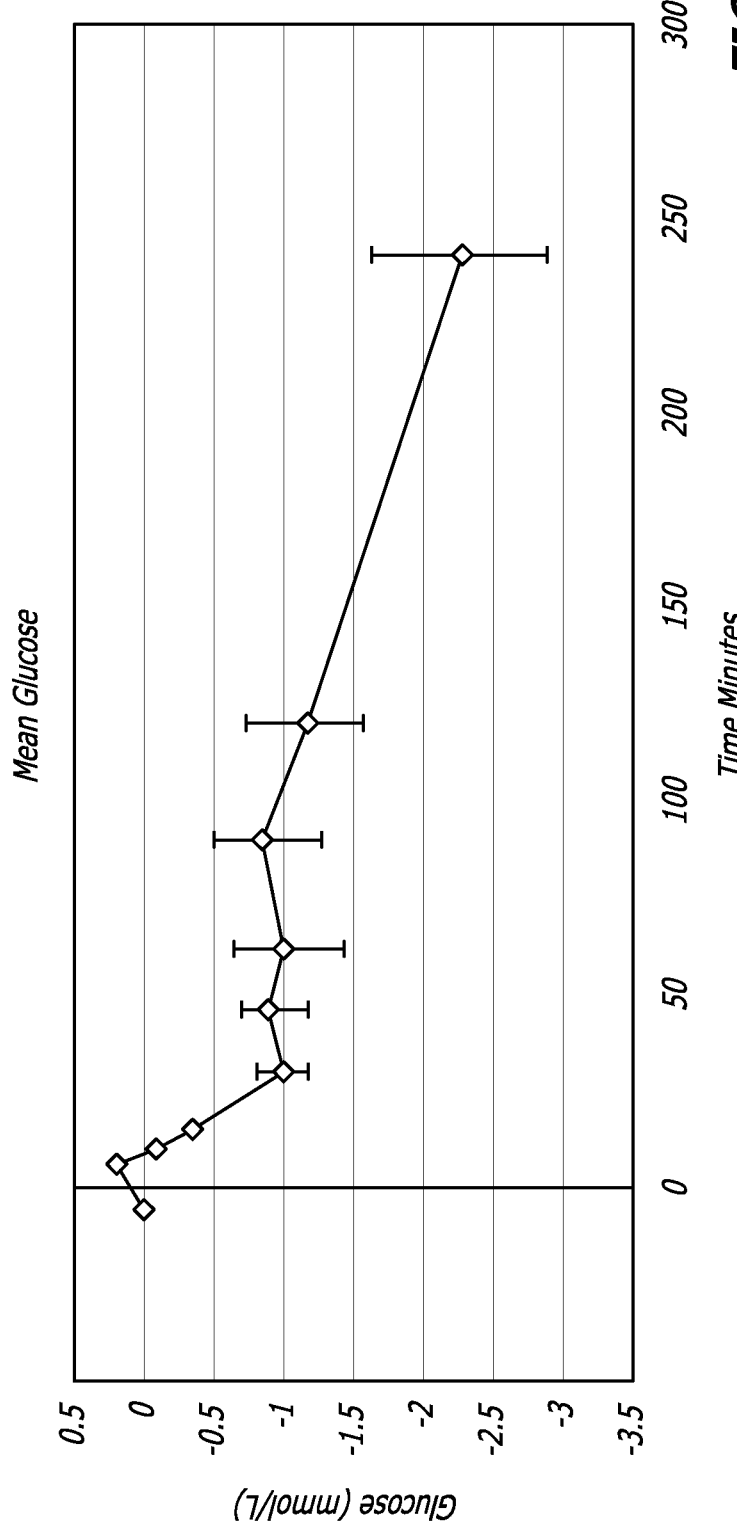
FIG. 12 depicts the mean glucose values for the group of six fasted Type 2 diabetic patients of FIG. 11, in which the glucose values are expressed as the change of glucose levels from zero time (dosing) for all six patients.

FIG. 12 is a graph showing the mean glucose values for the group of six fasted patients with Type 2 diabetes whose glucose values are shown in FIG. 11. In FIG. 12, the glucose values are expressed as the mean change of glucose levels from zero time (dosing) for all six patients. FIG. 12 shows a mean glucose drop of approximately 1 mmol/L, which is approximately equivalent to from about 18 mg/dL to about 20 mg/dL, is attained by the 30 min time point. This mean drop in glucose levels to last for 120 min. The changes are larger in subjects with higher baseline glucose and more prolonged, whereas in 2 of the 6 subjects, those subjects with the lowest baseline fasted blood glucose, showed only a transient lowering of glucose levels in this timeframe (data not shown). It was noted that those with higher fasting glucose do not typically have the same insulin response as those with lower values, so that when stimulated, those subjects with higher fasting glucose typically exhibit a greater response than those whose glucose value are closer to normal.

Example 5

First Pass Distribution Model of Intact GLP-1 to Brain and Liver

First pass distribution of GLP-1 through the systemic circulation following pulmonary delivery and intravenous bolus administration was calculated to determine the efficacy of delivery for both methods of GLP-1 administration. A model was developed based on the assumptions that: (1) the absorption of GLP-1 from the lungs and into the pulmonary veins exhibited zero-order kinetics; (2) the distribution of GLP-1 to the brain and within the brain occurs instantaneously, and (3) clearance of GLP-1 from the brain and liver distribution is driven by basal blood flow only. Based on these assumptions, the analysis to determine the amount of GLP-1 in the brain and liver was based on published data with respect to extraction of GLP-1 by certain tissues and organs (Deacon, C. F. et al. "Glucagon-like peptide 1 undergoes differential tissue-specific metabolism in the anesthetized pig." American Physiological Society, 1996, pages E458-E464), and blood flow distribution to the body and rate due to cardiac output from human studies (Guyton Textbook of Physiology, $10^{th}$ Edition; W. B. Saunders, 2000, page 176). In a normal subject (70 kg) having normal physiological parameters such as blood pressure at resting, the basal flow rate to the brain and liver are 700 mL/min and 1350 mL/min, respectively. Based on cardiac output, blood flow distribution to the body has been calculated to be 14% to the brain, 27% to the liver and 59% to remaining body tissues (Guyton).

Using the above-mentioned parameters, the relative amounts of GLP-1 that would be distributed to the brain and liver for a 1 mg dose given by pulmonary and intravenous administration were determined. One mg of GLP-1 was divided by 60 seconds, and the resultant number was multiplied by 14% flow distribution to the brain. Therefore, every second a fraction of the dose is appearing in the brain. From the data available indicating that blood in the brain is equal to 150 mL and the clearance rate is 700 mL/min, the calculations on clearance of GLP-1 yields about 12 mL/second, which equals approximately 8% of the blood volume being cleared from the brain per second. In the intravenous studies in pigs reported by Deacon et al., 40% of GLP-1 was instantaneously metabolized in the vein and 10% was also metabolized in the deoxygenated blood in the lung. Accordingly, 40% followed by another 10% of the total GLP-1 was subtracted from the total amount administered in the calculations with respect to the intravenous data analysis.

For the GLP-1 amounts estimated in the liver, the same degradation assumptions were made for the intravenous and pulmonary administration routes, with 40% followed by another 10% total amount loss for the IV dose. Twenty-seven percent of the remaining GLP-1 was assumed to be distributed to the liver, with 75% of the blood passing through the portal bed first. Instantaneous distribution of blood in the liver was assumed. Calculations were as follows: One mg of GLP-1 was divided by 60 seconds, 40% followed by another 10% of the total GLP-1 was subtracted from the total amount administered with respect to the intravenous data analysis. No degradation was assumed for the pulmonary administration. The resultant numbers were multiplied by 27% flow distribution to the liver, for both routes of administration, with 75% of this amount passing though the portal bed first. In the intravenous studies in pigs reported by Deacon et al., 20% extraction by the portal bed was reported; hence 75% of the amount of GLP-1 was reduced by 20% before being introduced into the liver. Therefore, the total amount of GLP-1 appearing in the liver every second is comprised of a fraction which has undergone metabolism in the portal bed. From the data available indicating that blood volume in the liver is equal to 750 mL and the clearance rate is 1350 mL/minute, the calculations on clearance of GLP-1 yields about 22.5 mL/second, which equals approximately 3% of the blood volume being cleared from the liver per second. Deacon et al. reported 45% degradation in the liver, accordingly, 45% of the total GLP-1 was subtracted from the total amount appearing in the liver, and the remainder was added to the total remaining amount.

The results of the calculations described above are presented in Tables 4 and 5. The calculated GLP-1 distribution in brain and liver after pulmonary administration (Table 4) are shown below:

TABLE 4

| Pulmonary administration of 1 mg GLP-1 | | |
| --- | --- | --- |
| Time in Seconds | Brain (µg) | Liver (µg) |
| 1 | 2.3 | 2.10 |
| 5 | 9.94 | 9.91 |
| 60 | 29.0 | 58.9 |

The results illustrating the distribution of GLP-1 after an intravenous bolus administration are shown in Table 5 below:

TABLE 5

Intravenous bolus administration of 1 mg GLP-1 over 1 minute

| Time in Seconds | Brain (μg) | Liver (μg) |
|---|---|---|
| 1 | 1.26 | 1.14 |
| 5 | 5.37 | 5.35 |
| 60 | 15.6 | 31.7 |

The data above are representative illustrations of the distribution of GLP-1 to specific tissues of the body after degradation of GLP-1 by endogenous enzymes. Based on the above determinations, the amounts of GLP-1 in brain and liver after pulmonary administration are about 1.82 to about 1.86 times higher than the amounts of GLP-1 after intravenous bolus administration. Therefore, the data indicate that pulmonary delivery of GLP-1 can be a more effective route of delivery when compared to intravenous administration of GLP-1, as the amount of GLP-1 at various times after administration would be about double the amount obtained with intravenous administration. Therefore, treatment of a disease or disorder comprising GLP-1 by pulmonary administration would require smaller total amounts, or almost half of an intravenous GLP-1 dose that is required to yield the same or similar effects.

Example 6

The studies in this example were conducted to measure the pharmacokinetic parameters of various active agents by subcutaneous administration and in formulations comprising a FDKP, FDKP disodium salt, succinyl-substituted-DKP (SDKP, also referred to herein as Compound 1) or asymmetrical (fumaryl-monosubstituted)-DKP (also referred herein as Compound 2) to ZDF rats administered by pulmonary insufflation. The rats were divided into 8 groups and five rats were assigned to each group. Each rat in Group 1 received a 0.3 mg dose of exendin-4 in phosphate buffered saline solution by pulmonary liquid instillation; Group 2 received 0.3 mg of exendin-4 in phosphate buffered saline by subcutaneous injection.

Rats in Groups 3-8 received their dosing of active agent or exendin-4 by pulmonary insufflation as follows: Group 3 rats received a 2 mg formulation of GLP-1/FDKP by pulmonary insufflation, followed by a 2 mg dose of exendin-4; Group 4 received a formulation of exendin-4/FDKP; Group 5 rats received a 3 mg dose of exendin-4 formulated as a 9.2% load in a disodium salt of FDKP; Group 6 rats received a 2 mg dose of exendin-4 formulated as a 13.4% load in a disodium salt of FDKP; Group 7 rats received a 2 mg dose of exendin-4 formulated as a 14.5% load in SDKP, and Group 8 rats received a 2 mg dose of exendin-4 formulated as a 13.1% load in asymmetrical (fumaryl-mono-substituted) DKP.

Figure 13:
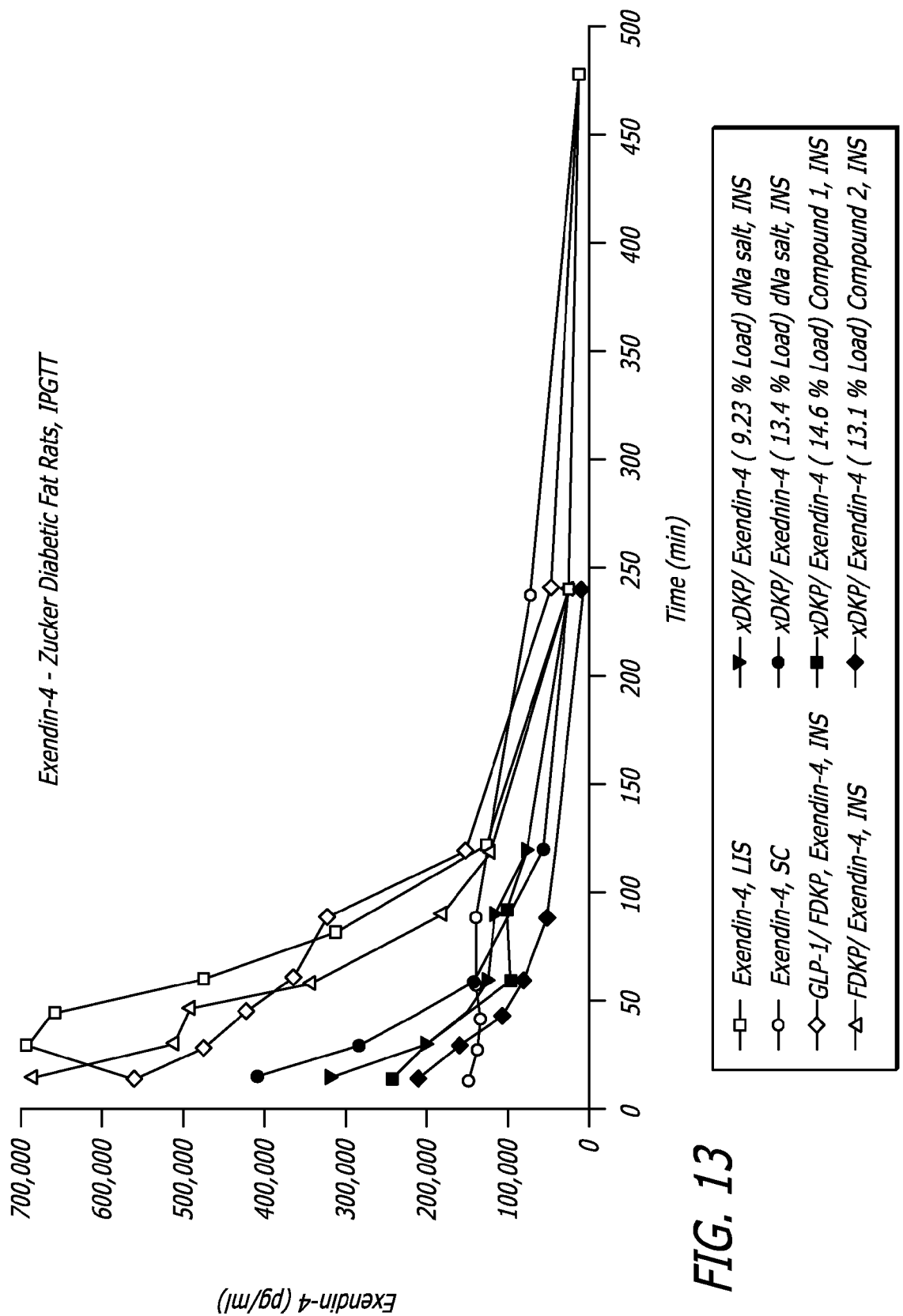
FIG. 13 depicts data obtained from experiments in which ZDF rats were administered exendin-4 in a formulation comprising a diketopiperazine or a salt of a diketopiperazine, wherein the exendin-4 was provided by various routes of administration (liquid installation (LIS), SC, pulmonary insufflation (INS)) in an intraperitoneal glucose tolerance test (IPGTT). In one group, rats were treated with exendin-4 in combination with GLP-1 by pulmonary insufflation.

The dosing of the animals occurred over the course of two days to accommodate the high numbers of subjects. The various test articles were administered to the animals and blood samples were taken at various times after dosing. Exendin-4 concentrations were measured in plasma isolates; the results for which are provided in FIG. 13. As depicted in the graph, Group 4 treated rats which received exendin-4 in a formulation containing FDKP exhibited high levels of exendin-4 in the blood earlier than 30 min and at higher levels than the rats in Group 2, which received exendin-4 by subcutaneous administration. In all groups, the levels of exendin-4 decrease sharply at about an hour after administration.

Administration of exendin-4/FDKP by pulmonary insufflation in ZDF rats has similar dose-normalized $C_{max}$, AUC, and bioavailability as exendin-4 administered as a subcutaneous injection. Exendin-4/FDKP administered by pulmonary insufflation showed a greater than two-fold half life compared to exendin-4 by subcutaneous injection. Exendin-4 administered as an fumaryl(mono-substituted)DKP, or SDKP formulation showed lower dose normalized $C_{max}$, AUC, and bioavailability compared to subcutaneous injection (approximately 50% less) but higher levels than pulmonary instillation.

After an overnight fast, ZDF rats were given a glucose challenge by intraperitoneal injection (IPGTT). Treatment with exendin-4/FDKP showed a greater reduction in blood glucose levels following the IPGTT compared to exendin-4 by the subcutaneous route. Compared to air control animals, blood glucose levels were significantly lowered following an IPGTT for 30 and 60 min in animals administered exendin-4 by subcutaneous injection and exendin-4/FDKP powder by pulmonary administration, respectively. Group 3 ZDF rats treated with exendin-4/FDKP and GLP-1 by pulmonary insufflation after treatment with intraperitoneal glucose administration (IPGTT) showed surprisingly lower blood glucose levels following IPGTT compared to either treatment alone at 30 min post dose (−28% versus −24%).

Example 7

The studies in this example were conducted to measure the pharmacokinetic and pharmacodynamic profile of peptide YY(3-36) formulations by pulmonary administration to ZDF rats compared to intravenous injections.

Preparation of PYY/FDKP formulation for pulmonary delivery: Peptide YY(3-36) (PYY) used in these experiments was obtained from American Peptide and was adsorbed onto FDKP particles as a function of pH. A 10% peptide stock solution was prepared by weighing 85.15 mg of PYY into an 8 ml clear vial and adding 2% aqueous acetic acid to a final weight of 762 mg. The peptide was gently mixed to obtain a clear solution. FDKP suspension (4968 mg, containing 424 mg of FDKP preformed particles) was added to the vial containing the PYY solution, which formed a PYY/FDKP particle suspension. The sample was placed on a magnetic stir-plate and mixed thoroughly throughout the experiment. A micro pH electrode was used to monitor the pH of the mixture. Aliquots of 2-3 μL of a 14-15% aqueous ammonia solution were used to incrementally increase the pH of the sample. Sample volumes (75 μL for analysis of the supernatant; 10 μL for suspension) were removed at each pH point. The samples for supernatant analysis were transferred to 1.5 ml, 0.22 μm filter tubes and centrifuged. The suspension and filtered supernatant samples were transferred into HPLC autosampler vials containing 990 μL of 50 mM sodium bicarbonate solution. The diluted samples were analyzed by HPLC to assess the characteristics of the preparations. The experiments indicated that, for example, a 10.2% of PYY solution can be adsorbed onto FDKP particles at pH 4.5 In this particular preparation, for example, the PYY content of the resultant powder was determined by HPLC to be 14.5% (w/w). Cascade measurements of aerodynamic characteristics of the powder showed a respirable fraction of 52% with a 98% cartridge emptying when discharged through the MED-TONE® dry powder inhaler (MannKind Corporation). Based on the results above, multiple sample preparations of PYY/FDKP powder were made, including, 5%, 10%, 15% and 20% PYY.

Pharmacokinetic and pharmacodynamic studies: Female ZDF rats were used in these experiments and divided into 7 groups; five rats were assigned to each group, except for Group 1 which had 3 rats. The rats were fasted for 24 hr prior to being given their assigned dose and immediately provided with food after dosing and allowed to eat as desired for the period of the experiment. Each rat in Group 1 received a 0.6 mg IV dose of PYY in phosphate buffered saline solution; Group 2 rats received 1.0 mg of PYY pulmonary liquid instillation; Group 3 rats were designated as control and received a stream of air; Groups 4-7 rats received a dry powder formulation for inhalation administered by pulmonary insufflation as follows: Group 4 rats received 0.15 mg of PYY in a 3 mg PYY/FDKP powder formulation of 5% PYY (w/w) load; Group 5 rats received 0.3 mg of PYY in a 3 mg PYY/FDKP powder formulation of 10% PYY (w/w) load; Group 6 rats received 0.45 mg of PYY in a 3 mg PYY/FDKP powder formulation of 15% PYY (w/w) load; Group 7 rats received 0.6 mg of PYY in a 3 mg PYY/FDKP powder formulation of 20% PYY (w/w) load.

Figure 14:
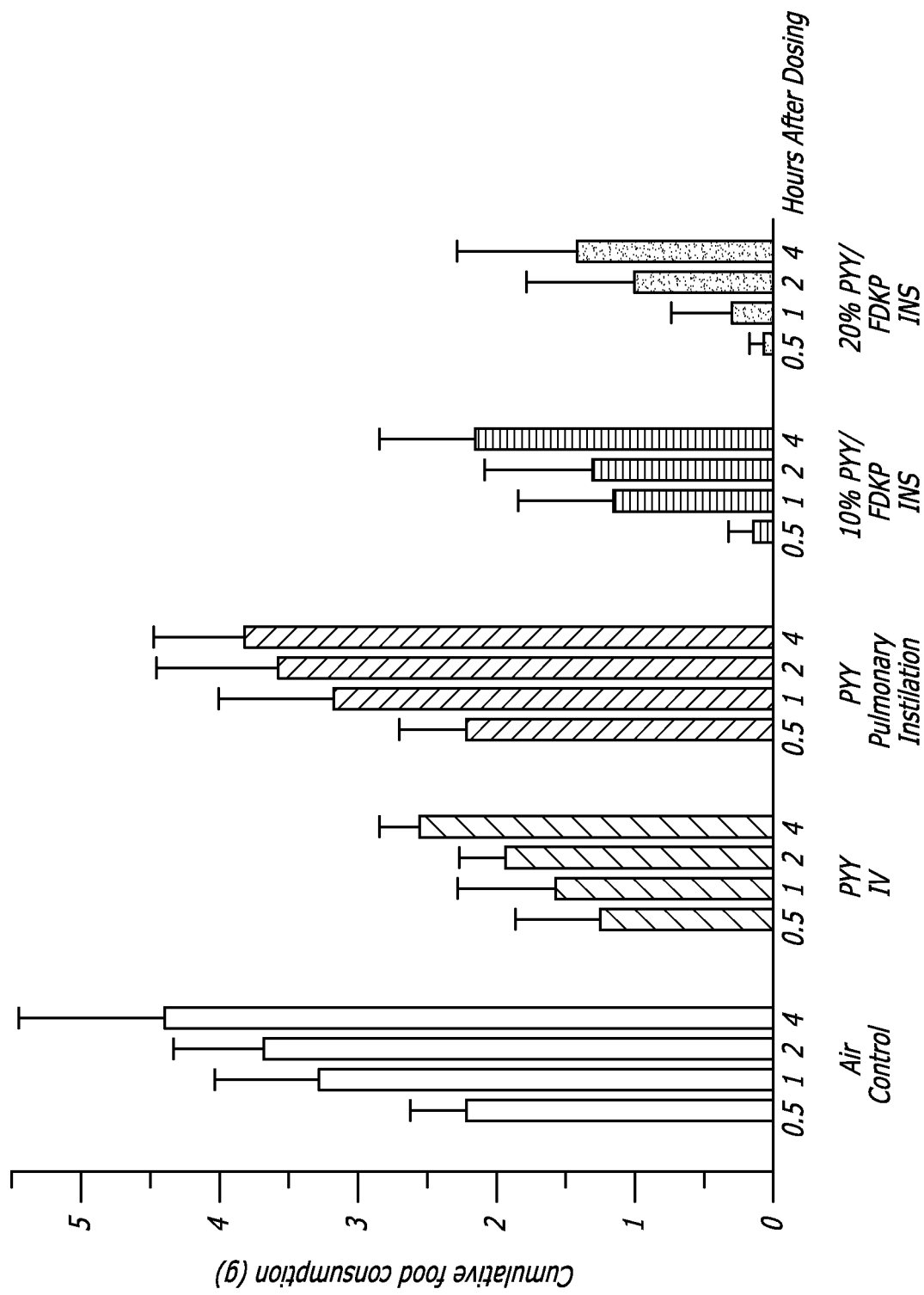
FIG. 14 depicts cumulative food consumption in male ZDF rats receiving air control by pulmonary insufflation, protein YY(3-36) (PYY) alone by IV injection, PYY alone by pulmonary instillation, 10% PYY/FDKP powder (0.3 mg PYY) by pulmonary insufflation; 20% PYY/FDKP powder (0.6 mg PYY) by pulmonary insufflation. For each group food consumption was measured 30 minutes after dosing, 1 hour after dosing, 2 hours after dosing, and 4 hours after dosing. Data are plotted mean±SD.
Figure 15:
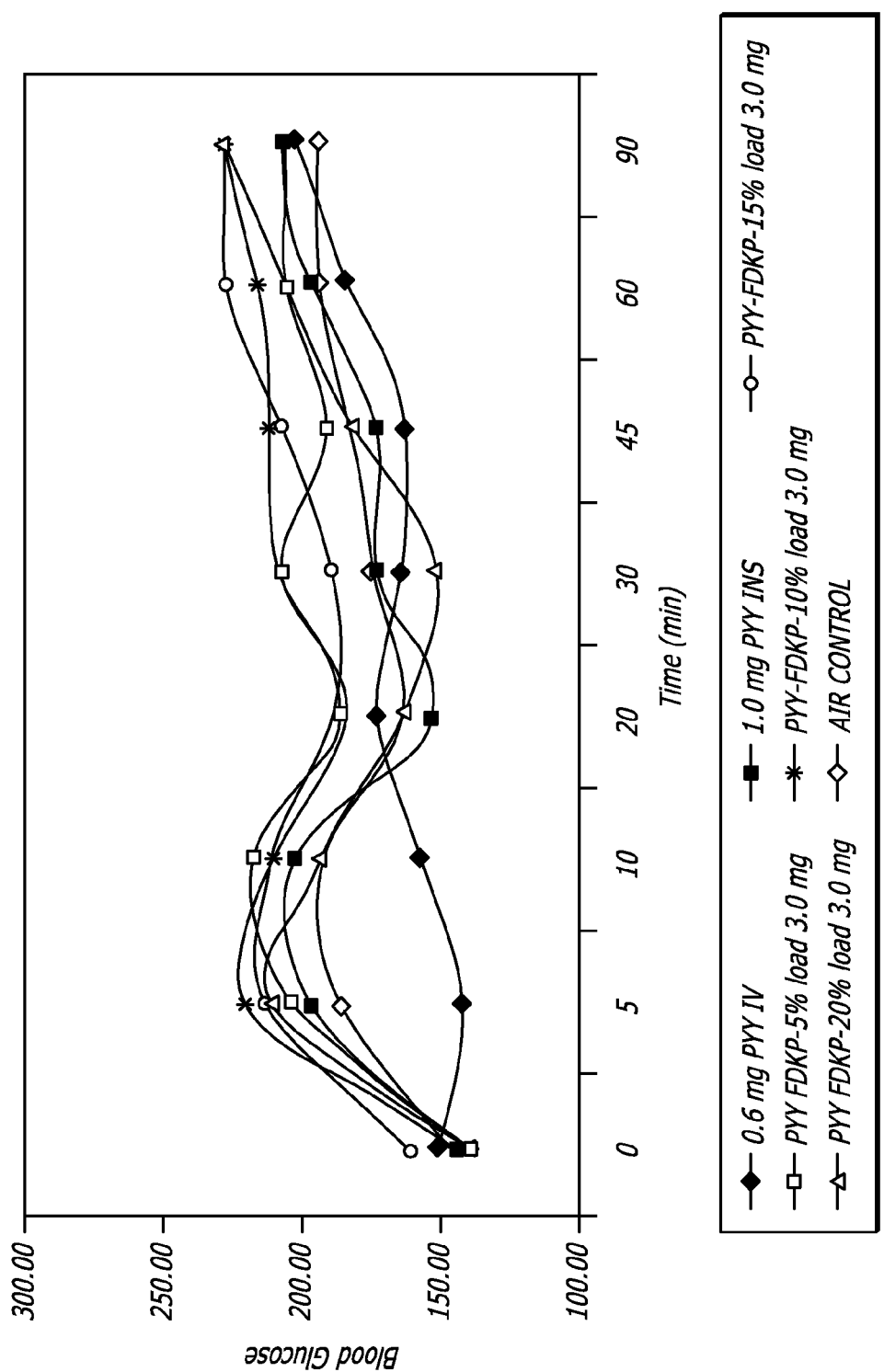
FIG. 15 depicts the blood glucose concentration in female ZDF rats administered PYY/FDKP powder by pulmonary insufflation versus intravenously administered PYY at various times following dose administration.
Figure 16:
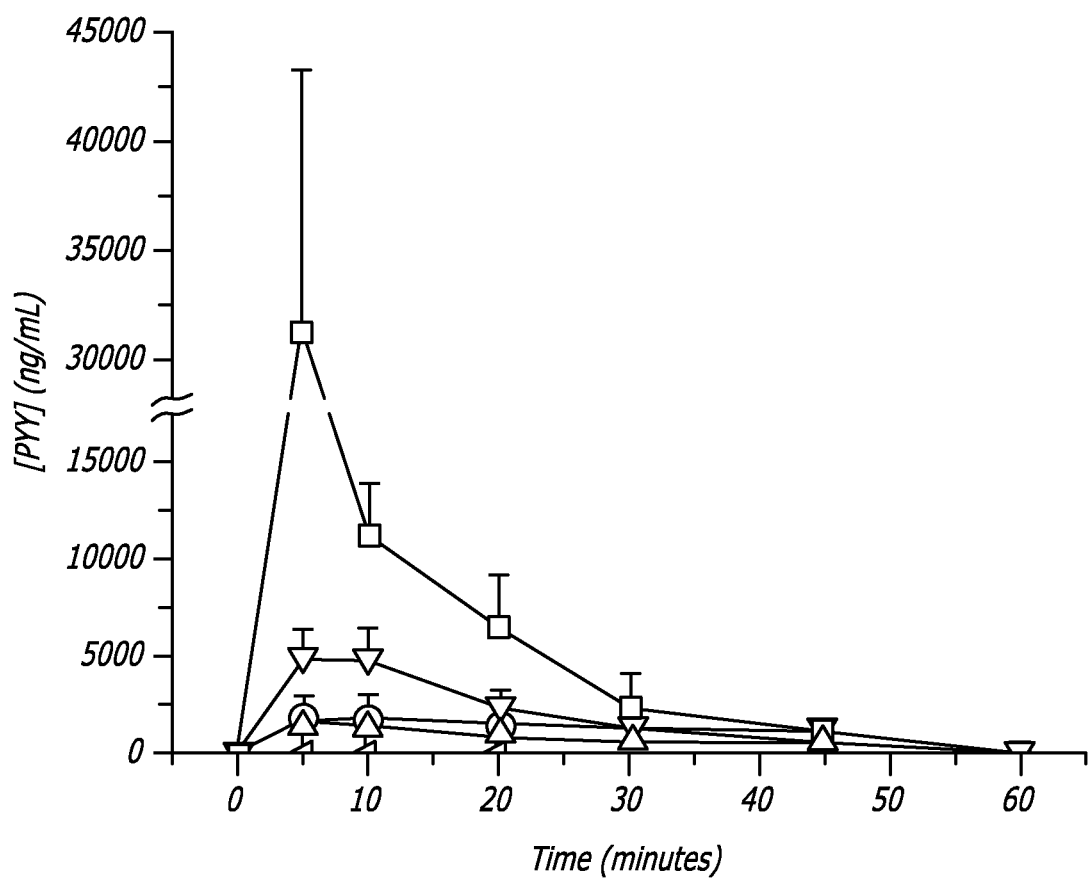
FIG. 16 depicts mean plasma concentrations of PYY in female ZDF rats receiving PYY/FDKP powder by pulmonary insufflation versus intravenously administered PYY. The squares represent the response following intravenous administration of PYY alone (0.6 mg). The circles represent the response following liquid instillation of PYY alone (1 mg). The down triangles represent the response following pulmonary insufflation of 20% PYY/FDKP powder (0.6 mg PYY). The up triangles represent the response following pulmonary insufflation of 10% PYY/FDKP powder (0.3 mg PYY). The left-pointing triangles represent the response following pulmonary insufflation of air alone. Data are plotted as ±SD.

Food consumption was measured for each rat at 30, 60, 90, 120, 240 min and 24 hr after dosing. PYY plasma concentrations and glucose concentrations were determined for each rat from blood samples taken from the rats before dosing and at 5, 10, 20, 30, 45, 60 and 90 min after dosing. The results of these experiments are shown in FIGS. 14-16 and Table 6 below. FIG. 14 is a bar graph of representative data from experiments measuring food consumption in female ZDF rats receiving PYY formulations by intravenous administration and by pulmonary administration in a formulation comprising a fumaryl-diketopiperazine at the various doses. The data show that food consumption was reduced for all PYY-treated rats when compared to control with the exception of Group 2 which received PYY by instillation. Reduction in food consumption by the rats was statistically significant for the rats treated by pulmonary insufflation at 30, 60, 90 and 120 min after PYY-dosing when compared to control. The data in FIG. 14 also show that while IV administration (Group 1) is relatively effective in reducing food consumption in the rats, the same amount of PYY (0.6 mg) administered by the pulmonary route in an FDKP formulation (Group 7) was more effective in reducing the amount of food intake or suppressing appetite for a longer period of time. All PYY-treated rats receiving pulmonary PYY-FDKP powders consumed less food when compared to controls.

FIG. 15 depicts the measured blood glucose levels in the female ZDF rats given PYY formulations by IV administration; by pulmonary administration with various formulations comprising a fumaryl-diketopiperazine and air control rats. The data indicate the blood glucose levels of the PYY-treated rats by pulmonary insufflation remained relatively similar to the controls, except for the Group 1 rats which were treated with PYY IV. The Group 1 rats showed an initial lower blood glucose level when compared to the other rats up to about 15 min after dosing.

FIG. 16 depicts representative data from experiments measuring the plasma concentration of PYY in the female ZDF rats given PYY formulations by IV administration; by pulmonary administration with various formulations comprising a fumaryl-diketopiperazine, and air control rats taken at various times after administration. These measurements are also represented in Table 6. The data show that Group 1 rats which were administered PYY IV attained a higher plasma PYY concentration (30.7 µg/mL) than rats treated by pulmonary insufflation. Peak plasma concentration ($T_{max}$) for PYY was about 5 min for Groups 1, 6 and 7 rats and 10 min for Group 2, 4 and 5 rats. The data show that all rats treated by pulmonary insufflation with a PYY/FDKP formulation had measurable amounts of PYY in their plasma samples, however, the Group 7 rats had the highest plasma PYY concentration (4.9 µg/mL) and values remained higher than the other groups up to about 35 min after dosing. The data also indicate that the plasma concentration of PYY administered by pulmonary insufflation is dose dependent. While administration by IV injection led to higher venous plasma concentration of PYY that did pulmonary administration of PYY/FDKP at the dosages used, the greater suppression of food consumption was nonetheless achieved with pulmonary administration of PYY/FDKP.

TABLE 6

| Rat Group Number | T½ (min) | Tmax (min) | Cmax (µg/mL) | AUCall/D (min/mL) | BA (%) |
|---|---|---|---|---|---|
| 1 | 13 | 5 | 30.7 | 0.61 | 100% |
| 2 | 22 | 10 | 1.7 | 0.06 | 11 |
| 4 | 23 | 10 | 0.51 | 0.10 | 16 |
| 5 | 30 | 10 | 1.33 | 0.15 | 25 |
| 6 | 26 | 5 | 2.79 | 0.20 | 33 |
| 7 | 22 | 5 | 4.90 | 0.22 | 36 |

Figure 17:
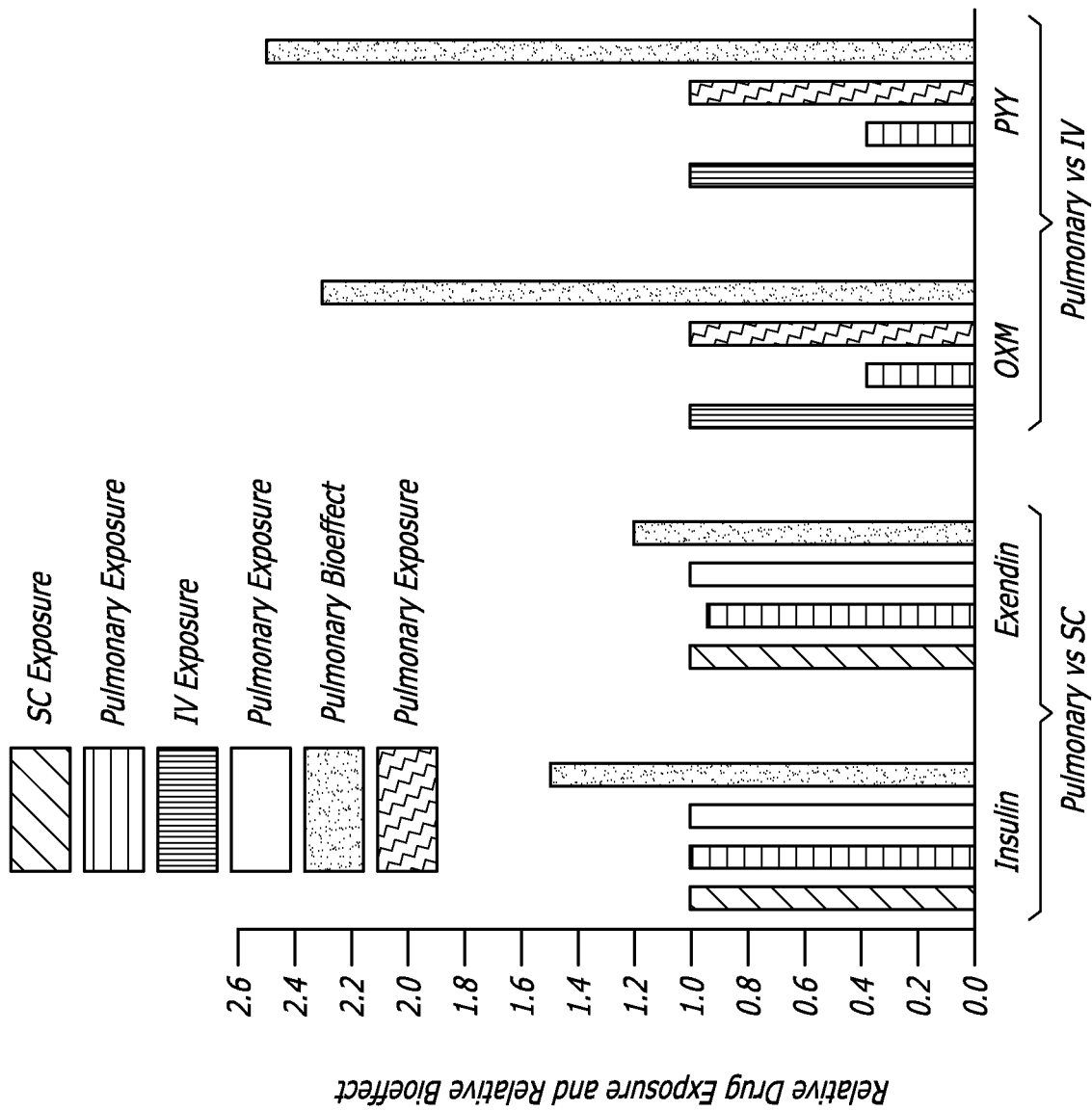
FIG. 17 depicts the relative drug exposure and relative bioeffect of the present formulations administered by pulmonary inhalation and containing insulin, exendin, oxyntomodulin or PYY compared to subcutaneous and intravenous administration.

FIG. 17 illustrates the effectiveness of the present drug delivery system as measured for several active agents, including insulin, exendin, oxyntomodulin and PYY and exemplified herewith. Specifically, FIG. 17 demonstrates the relationship between drug exposure and bioeffect of the pulmonary drug delivery system compared to IV and SC administration of the aforementioned active agents. The data in FIG. 17 indicate that the present pulmonary drug delivery system provides a greater bioeffect with lesser amounts of drug exposure than intravenous or subcutaneous administration. Therefore, lesser amounts of drug exposure can be required to obtain a similar or greater effect of a desired drug when compared to standard therapies. Thus, in one embodiment, a method of delivering an active agent, including, peptides such as GLP-1, oxyntomodulin, PYY, for the treatment of disease, including diabetes, hyperglycemia and obesity which comprises administering to a subject in need of treatment an inhalable formulation comprising one or more active agents and a diketopiperazine whereby a therapeutic effect is seen with lower exposure to the active agent than required to achieve a similar effect with other modes of administration. In one embodiment, the active agents include peptides, proteins, lipokines.

Example 8

Assessment of GLP-1 Activity in Postprandial Type 2 Diabetes Mellitus

The purpose of this study was to evaluate the effect of a GLP-1 dry powder formulation on postprandial glucose concentration and assess its safety including adverse events, GPL-1 activity, insulin response, and gastric emptying.

Experimental Design: The study was divided into two periods and enrolled 20 patients diagnosed with type 2 diabetes ranging in age from 20 to 64 years of age. Period 1 was an open-label, single-dose, trial in which 15 of the patients received a dry powder formulation comprising 1.5 mg of GLP-1 in FDKP administered after having fasted overnight. As control, 5 subjects received FDKP inhalation powder after fasting overnight. Period 2 was performed after completion of Period 1. In this part of the study, the patients were given 4 sequential treatments each with a meal challenge consisting of 475 Kcal and labeled with $^{13}$C-octanoate as marker. The study was designed as a double-blind, double dummy, crossover, meal challenge study, in which saline as control and exenatide were given as injection 15 minutes before a meal and dry powder formulations of inhalable GLP-1 or placebo consisting of a dry powder formulation without GLP-1, were administered immediately before the meal and repeated 30 minutes after the meal. The four treatments were as follows: Treatment 1 consisted of all patients receiving a placebo of 1.5 mg of dry powder formulation without GLP-1. In Treatment 2, all patients received one dose of 1.5 mg of GLP-1 in a dry powder formulation comprising FDKP. In Treatment 3, all patients received two doses of 1.5 mg of GLP-1 in a dry powder formulation comprising FDKP, one dose immediately before the meal and one dose 30 minutes after the meal. In Treatment 4, the patients received 10 μg of exenatide by subcutaneous injection. Blood samples from each patient were taken at various times before and after dosing and analyzed for several parameters, including GLP-1 concentration, insulin response, glucose concentration and gastric emptying. The results of this study are depicted in FIGS. 18-20.

Figure 18:
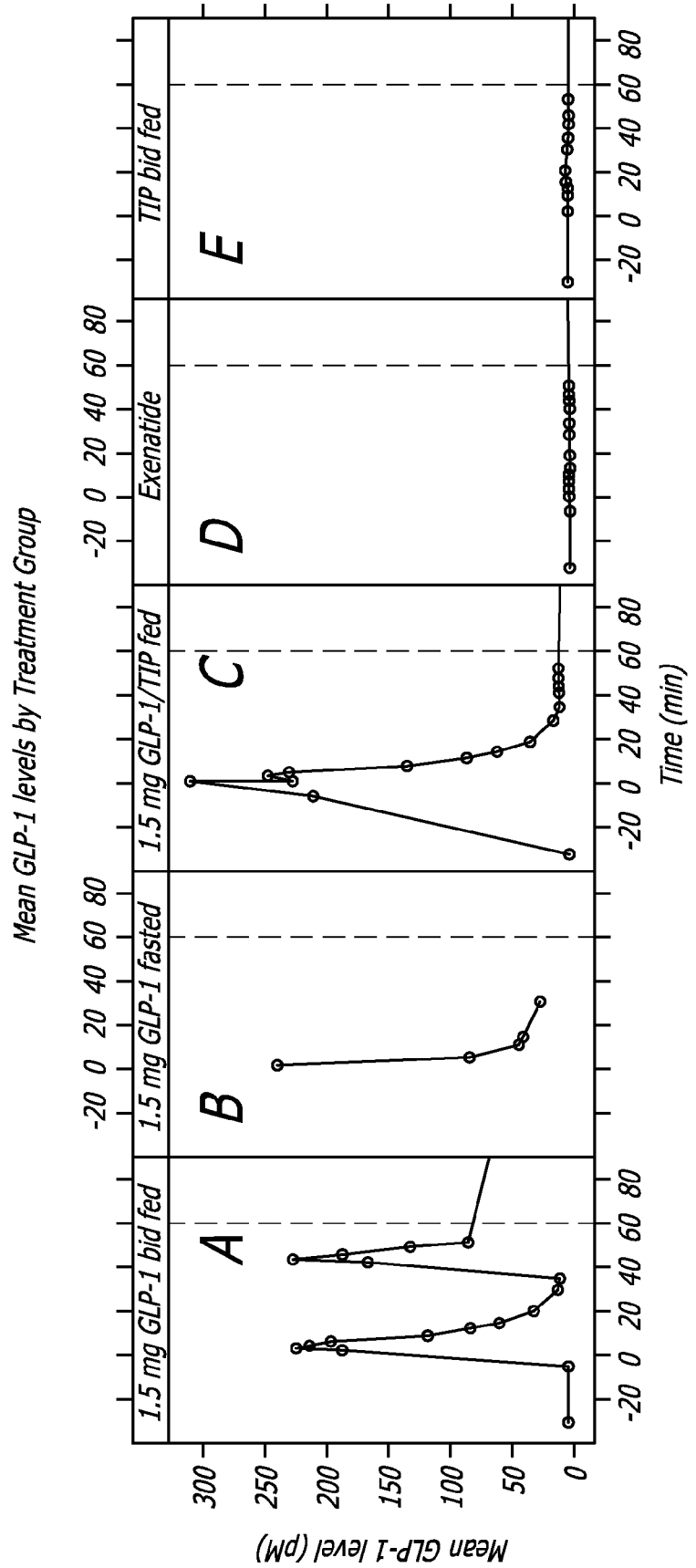
FIG. 18 depicts mean GLP-1 plasma levels in patients administered various inhaled GLP-1 and control formulations.

FIG. 18 depicts the mean GLP-1 levels in blood by treatment group as described above. The data demonstrate that the patients receiving the dry powder formulation comprising 1.5 mg of GLP-1 in FDKP had significantly higher levels of GLP-1 in blood soon after administration as shown in panels A, B and C and that the levels of GLP-1 sharply declined after administration in fed or fasted individuals. There were no measurable levels of GLP-1 in the exenatide-treated group (Panel D), or in controls (Panel E) receiving the dry powder formulation.

Figure 19:
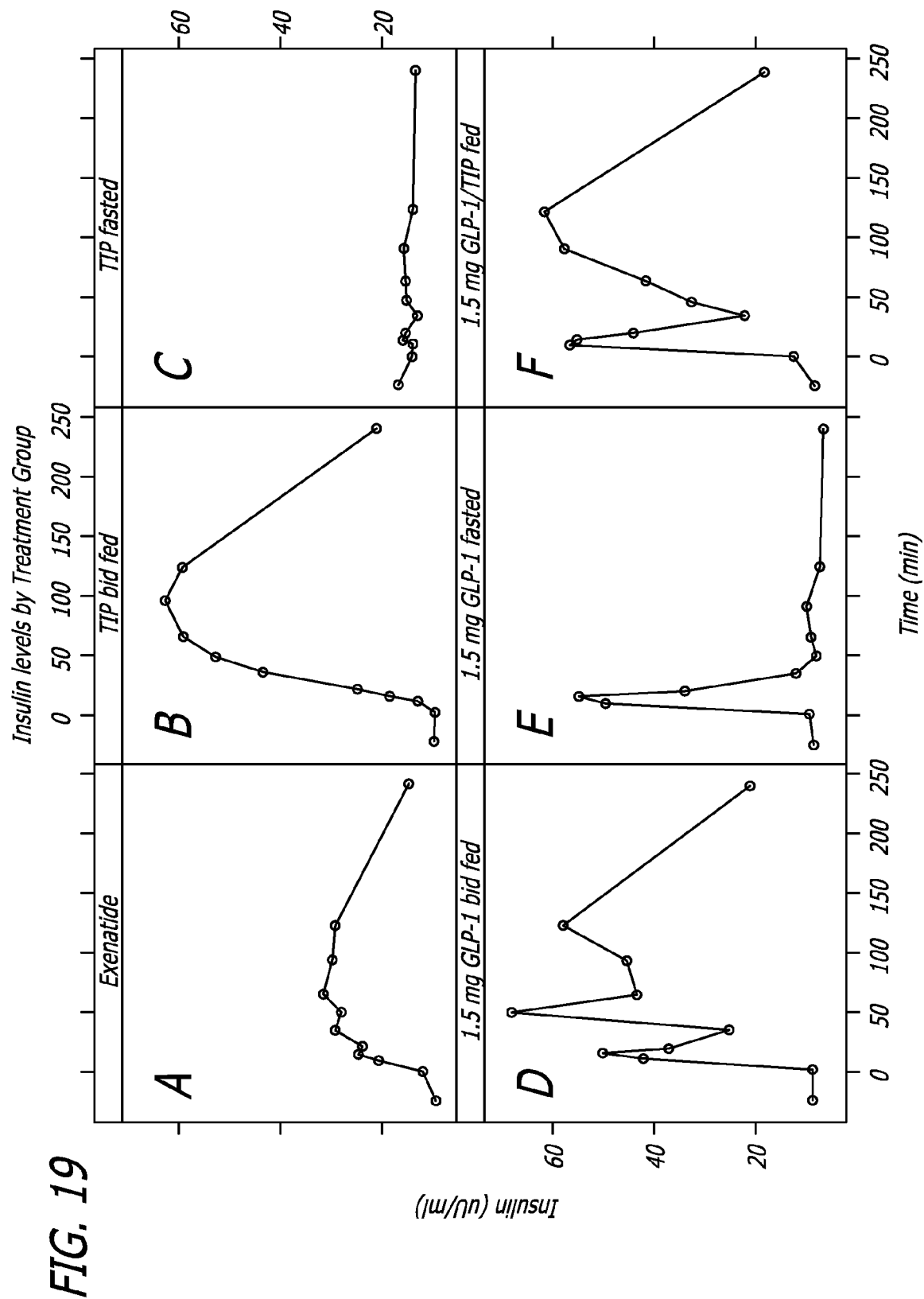
FIG. 19 depicts plasma insulin levels in patients administered various inhaled GLP-1 and control formulations.

FIG. 19 depicts the insulin levels of the patients in the study before or after treatment. The data show that endogenous insulin was produced in all patients after treatment including the placebo-treated patients in the meal challenge studies (Panel B), except for the fasted control patients (Panel C) who received the placebo. However, the insulin response was more significant in patients receiving GLP-1 in a dry powder composition comprising FDKP, in which the insulin response was observed immediately after treatment in both fed and fasted groups (Panels D-F). In fasted subjects, mean peak endogenous insulin release was approximately 60 μU/mL after GLP-1 administration by pulmonary delivery (Panel E). The results also showed that the glucose levels were reduced in patients treated with the dry powder formulation of GLP-1. Administration of the dry powder formulation of GLP-1 resulted in a delayed rise in blood glucose and reduced overall exposure (AUC) to glucose. Both the delayed rise and lessened exposure were more pronounced in subjects receiving a second administration of GLP-1 inhalation powder (data not shown). The magnitude of insulin release varied among patients, with some showing small but physiologically relevant levels of insulin whereas others exhibited much larger insulin releases. Despite the difference in insulin response between the patients, the glucose response was similar. This difference in insulin response may reflect variations in degree of insulin resistance and disease progression. Assessment of this response can be used as a diagnostic indicator of disease progression with larger releases (lacking greater effectiveness at controlling blood glucose levels) indicating greater insulin resistance and disease progression.

Figure 20:
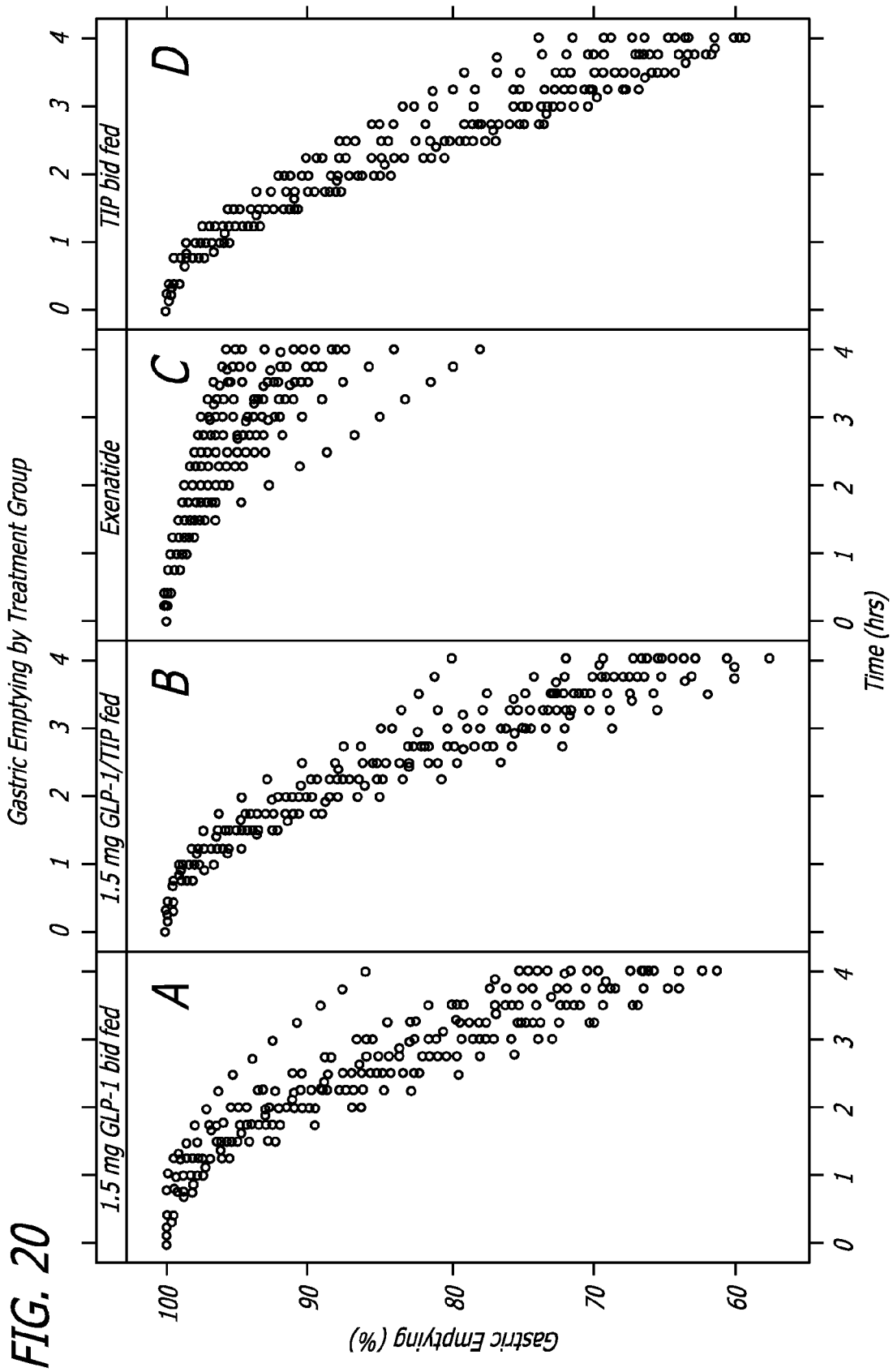
FIG. 20 depicts gastric emptying in response to an inhaled GLP-1 formulation in patients administered various inhaled GLP-1 and control formulations.

FIG. 20 depicts the percent gastric emptying by treatment groups. Panel A (patients in Treatment 3) and Panel B (patients in Treatment 2) patients had similar gastric emptying characteristics or percentages as the control patients shown in Panel D (Placebo treated patients with a dry powder formulation comprising FDKP without GLP-1). The data also show that patients treated with exenatide even at a 10 μg dose exhibited a significant delay or inhibition in gastric emptying when compared to controls. More than 90% of the $^{13}$C from the $^{13}$C-octanoate ingested was unabsorbed into the body 4 hours after the meal. In contrast, less than 60% of the $^{13}$C-octanoate ingested was unabsorbed in patients treated with inhaled GLP-1/FDKP at 4 hours after the meal. The data also demonstrate that the present system for delivering active agents comprising FDKP and GLP-1 lacks inhibition of gastric emptying; induces a rapid insulin release following GLP-1 delivery and causes a reduction in glucose AUC levels.

Example 9

Response to GLP-1 Administration is Dependent on Baseline Glucose Levels

Figure 21:
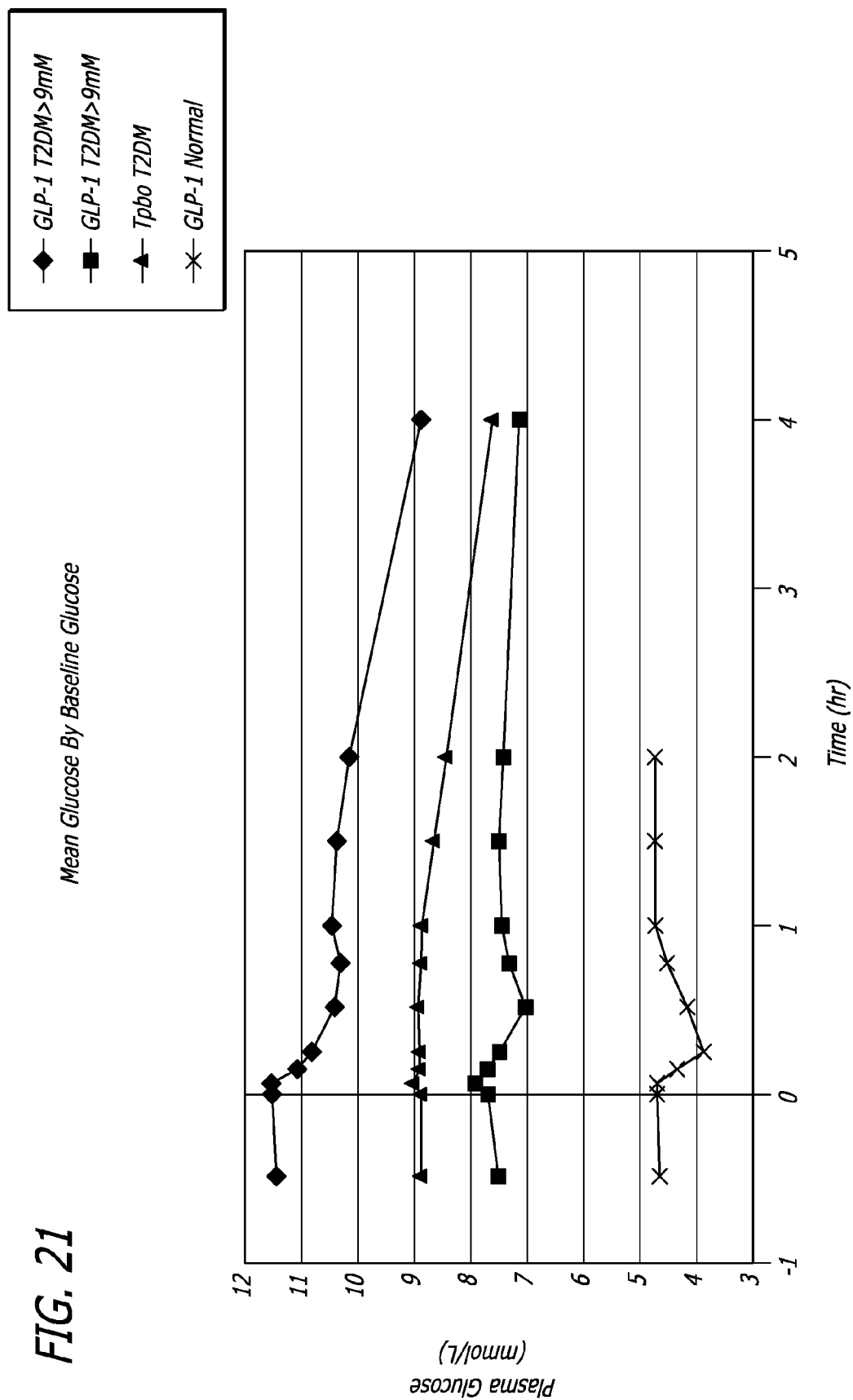
FIG. 21 depicts mean plasma glucose levels of fasting normal subjects, and subjects with type 2 diabetes mellitus given inhaled GLP-1 formulations or placebo.

In this example, data are presented from the studies presented in Examples 1 and 8 described above, in which GLP-1 was administered to normal fasting subjects, and to subjects with Type 2 diabetes (T2DM). All subjects were non-smokers with normal lung function. Subjects received 1.5 mg GLP-1 in a formulation comprising FDKP via inhalation while fasting. In the first study, 6 normal subjects received GLP-1. In the second study, 15 subjects with T2DM received GLP-1, and 5 subjects with T2DM received placebo. Blood glucose levels in all subjects were measured as described in Examples 1 and 8 above and the data are presented in FIG. 21.

In normal subjects, controls showed baseline glucose levels ranging from about 4 mmol/L to about 5 mmol/L throughout the experiment. GLP-1 administered by inhalation produced a transient decrease in glucose of 0.8 mmol/L. Minimum glucose levels occurred approximately 15 minutes after inhalation of the GLP-1 formulation. Following the decrease in glucose levels, glucose levels returned to baseline levels by 1 hr. The duration of response was much longer than the $t_{1/2}$ of GLP-1 ($\leq 2$ min).

Response to GLP-1 in subjects with T2DM depended on blood glucose concentration. Of the 15 subjects with T2DM who received GLP-1, 11 had baseline plasma glucose concentrations (BIGIu) greater than 9 mmol/L and 4 had BIGIu less than 9 mmol/L. Subjects with blood glucose levels less than 9 mmol/L had a mean maximum decrease of 0.75 mmol/L. The time to reach the minimum was about ½ hr. Although glucose values recovered, they had not return to baseline levels after 4 hr. Subjects with blood glucose levels greater than 9 mmol/L had a 1.2 mmol/L decrease in glucose. The duration of response was longer, since the minimum occurred 45 min after inhalation, with no return from the minimum levels. Placebo treated subjects had no change in glucose over the first 2 hrs after inhalation.

The data show that inhalation of GLP-1 in a formulation comprising a diketopiperazine produces a sharp spike or increase in plasma insulin in the subjects tested, which is indicative of endogenous insulin production in pancreatic β-cell. This rapid pulse of insulin can produce a long-lasting and more pronounced decline in plasma glucose concentration in subjects with T2DM having more elevated fasting plasma glucose levels.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A method for treating hyperglycemia, comprising the step of administering to a human subject having a fasting blood glucose concentration greater than about 7 mmol/L an inhalable dry powder formulation comprising microparticles comprising a therapeutically effective amount of a glucagon like peptide-1 (GLP-1) molecule and a diketopiperazine, wherein the GLP-1 molecule is a native GLP-1, a GLP-1 metabolite, a GLP-1 analog, a long acting GLP-1 analog, a GLP-1 mimetic, a GLP-1 peptide analog, a biosynthetic GLP-1 analog, or a combination thereof, wherein said GLP-1 has at least one biological activity of native GLP-1, and wherein said GLP-1 comprises GLP-1 in an amount from about 0.5 mg to about 3 mg of GLP-1 in the formulation and the formulation does not comprise a dipeptidyl-peptidase-IV (DPP-IV) inhibitor, and wherein the diketopiperazine is 2,5-diketo-3,6-di(4-X-aminobutyl)piperazine, wherein X is selected from the group consisting of succinyl, glutaryl, maleyl, and fumaryl; or a pharmaceutically acceptable salt thereof, and further wherein peak blood GLP-1 concentration is reached within about 20 minutes after administration.

2. The method of claim 1, wherein the patient is a mammal having Type 2 diabetes mellitus.

3. The method of claim 1 wherein the human subject has a fasting blood glucose concentration greater than about 9 mmol/L.

4. The method of claim 1 wherein X is fumaryl.

5. The method of claim 1, wherein the inhalable formulation is administered to said human subject prandially.

6. The method of claim 1 wherein the composition is administered pulmonarily.

7. A method for reducing glucose levels in a Type 2 diabetic patient, the method comprising the step of administering to said patient in need of treatment a dry powder inhalable formulation for pulmonary administration comprising microparticles comprising a therapeutically effective amount of a GLP-1, and a diketopiperazine or pharmaceutically acceptable salt thereof, wherein the Type 2 diabetic patient has a fasting blood glucose concentration greater than 8 mmol/L, wherein said GLP-1 comprises GLP-1 in an amount from about 0.5 mg to about 3 mg of GLP-1 in the formulation and the formulation does not comprise a DPP-IV inhibitor, and wherein the diketopiperazine is 2,5-diketo-3,6-di(4-X-aminobutyl)piperazine, wherein X is selected from the group consisting of succinyl, glutaryl, maleyl, and fumaryl, and further wherein peak blood GLP-1 concentration is reached within about 20 minutes after administration.

8. The method of claim 7, wherein the glucose levels are reduced by about 0.1 mmol/L to about 3 mmol/L for a period of approximately four hours after administration of said inhalable formulation to said Type 2 diabetic patient.

9. The method of claim 7, wherein the inhalable formulation is administered to said Type 2 diabetic patient prandially, preprandially, post-prandially or in a fasting state.

10. The method of claim 9, wherein the inhalable formulation is administered to said Type 2 diabetic patient prandially.

11. The method of claim 7 wherein the patient has a fasting blood glucose concentration greater than about 9 mmol/L.

12. The method of claim 7 wherein X is fumaryl.

* * * * *